US008048900B2

(12) United States Patent
Martin et al.

(10) Patent No.: US 8,048,900 B2
(45) Date of Patent: Nov. 1, 2011

(54) USE OF 15-LIPOXYGENASE INHIBITORS FOR TREATING OBESITY

(75) Inventors: Geneviève Martin, Loos (FR);
Sébastien Barradeau, Paris (FR);
Sakina Sayah-Jeanne, Lambersart (FR)

(73) Assignee: Genfit S.A., Loos (FR)

( * ) Notice: Subject to any disclaimer, the term of this patent is extended or adjusted under 35 U.S.C. 154(b) by 210 days.

(21) Appl. No.: 12/182,881

(22) Filed: Jul. 30, 2008

(65) Prior Publication Data

US 2009/0060905 A1    Mar. 5, 2009

Related U.S. Application Data

(63) Continuation of application No. PCT/FR2007/050711, filed on Jan. 30, 2007.

(30) Foreign Application Priority Data

Jan. 30, 2006    (FR) ...................................... 06 00828

(51) Int. Cl.
*A61K 31/425*    (2006.01)
*A61K 31/44*    (2006.01)
(52) U.S. Cl. .......................... 514/365; 514/342; 514/909
(58) Field of Classification Search .................. 514/365, 514/342, 909
See application file for complete search history.

(56) References Cited

U.S. PATENT DOCUMENTS

| 5,972,980 A | * | 10/1999 | Cornicelli et al. | ............. 514/365 |
| 7,351,727 B2 | * | 4/2008 | Weinstein | .................... 514/365 |

FOREIGN PATENT DOCUMENTS

| WO | WO 97/12613 | 4/1997 |
| WO | WO 99/17761 | 4/1999 |
| WO | WO 2004/112695 | 12/2004 |
| WO | WO 2006/044556 | 4/2006 |
| WO | WO 2007/085775 | 8/2007 |

OTHER PUBLICATIONS

Yokota et al., "Molecular biology and biochemistry of lipoxygenases and related pathways", New Horizons in Biotechnology, [International Conference on New Horizons in Biotechnology], Trivandrum, India, Apr. 18-21, 2001 (2003), Meeting Date 2001, 199-214 (enclosed abstract).*
Alberti, et al. (Sep. 24, 2005) "The metabolic syndrome—a new worldwide definition." Lancet 366(9491): 1059-1062.
Bray, et al. (Apr. 6, 2000) "Medicinal strategies in the treatment of obesity." Nature 404: 672-677.
Weinstein, et al. (Mar. 1, 2005) "Tryptamine and homotryptamine-based sulfonamides as potent and selective inhibitors of 15-lipoxygenase." Bioorganic & Medicinal Chemistry Letters 15(5): 1435-1440.
International Search Report dated Sep. 21, 2009 for International Application No. PCT/FR2007/050711.
Written Opinion dated Sep. 21, 2009 for International Application No. PCT/FR2007/050711.
Cornicelli JA et al, "15-Lipoxygenase and its inhibition: a novel therapeutic target for vascular disease", Curr Phram Des. Jan. 1999; 5(1);11-20 (PubMed Abstract).
Cichewicz et al, "Redox Inactivation of Human 15-Lipoxygenase by Marine-Derived Meroditerpenes and Synthetic Chromanes: Archetypes for a Unique Class of Selective and Recyclable Inhibitors", J. Am. Chem. Soc. 2004, 126, 14910-14920.
Segraves et al, "Probing the Activity Differences of Simple and Complex Brominated Aryl Compounds against 15-soybean, 15-Human, and 12-Human Lipoxygenase", J. Med. Chem. 2004, 47, 4060-4065.

* cited by examiner

*Primary Examiner* — Kevin E Weddington
(74) *Attorney, Agent, or Firm* — Nixon & Vanderhye P.C.

(57) ABSTRACT

The invention concerns the treatment of obesity, in particular abdominal visceral obesity. More specifically, the invention concerns the use of selective 15-lipoxygenase (LO) inhibitors for preparing medicines useful in the treatment of obesity, or at least abdominal visceral obesity, and/or its consequences.

4 Claims, 18 Drawing Sheets

Figure 1

USE OF 15-LIPOXYGENASE INHIBITORS FOR TREATING OBESITY

This application is a continuation of International Patent Application No. PCT/FR2007/050711, filed Jan. 30, 2007, which claims the benefit of French Patent Application No. FR 0600828, filed Jan. 30, 2006, the disclosures of each of which are hereby incorporated by reference.

The invention concerns the treatment of obesity, in particular abdominal visceral obesity. More specifically, the invention concerns the use of selective 15-lipoxygenase (LO) inhibitors for preparing medicines useful in the treatment of obesity, or at least abdominal visceral obesity, and its consequences.

INTRODUCTION

Obesity is an increasingly widespread chronic disease which has become a major public health problem in industrialized countries. The World Health Organization (WHO) recognizes obesity as the first non-infectious epidemic in history. The management of obesity is considered a priority, especially since excess weight is being seen at younger and younger ages.

Globally, obesity incidence have reached alarming levels. According to WHO data, close to half of all Americans are overweight, and one-quarter is clinically obese, a proportion that may be as high as 70% in some populations. In Europe, 30% of adults are overweight and 12% of adults in western Europe are obese. France has seen a 45% rise in obesity rates between 1987 and 1996, and an estimated 8 million individuals are obese. Obesity also affects the young: the number of obese children has doubled since the 1980s and the prevalence of obesity in children aged 6-12 years is estimated at 10-12%. Some studies predict that at this rate, obesity will affect half the European population by the year 2030.

Obesity is a condition characterized by an excess of adipose mass. The Body Mass Index (BMI), defined as weight in kilograms per square meter of height ($kg/m^2$), is an international standard for measuring excess weight and obesity. The BMI gives an indication of the degree of obesity and so allows an assessment of obesity-related health risks (see below). A person with a BMI greater than or equal to 30 $kg/m^2$ is considered obese. In addition to the BMI, it is also important to determine the bodily distribution of Adipose Tissue (AT). In fact, the increased adipose mass in obese individuals is found mainly in the intraabdominal and perivisceral regions of the trunk, and is known as abdominal visceral AT. Abdominal subcutaneous AT mass increases only marginally in obese subjects. This results in an increase in the ratio between abdominal visceral AT and abdominal subcutaneous AT. Even individuals who are not obese but who develop insulin resistance have a higher ratio of abdominal visceral AT to abdominal subcutaneous AT. Thus, according to the National Cholesterol Education Program—Adult Treatment Panel III (NCEP-ATP III), a waist circumference greater than 88 cm for women and 102 cm for men (variable according to ethnic group) is an indicator of abdominal visceral obesity and is associated with a higher risk of developing other health problems. The International Diabetes Federation (IDF) recently lowered the critical waist circumference thresholds to 80 cm in women and 94 cm in men (Alberti K G et al., 2005). This development of abdominal visceral AT is associated with a spectacular rise in cardiovascular risk (Larsson B et al., 1984) and (Lapidus L et al., 1984). Moreover, numerous epidemiological and metabolic studies have confirmed that a significant accumulation of AT in the abdominal region is a major risk factor for the development of metabolic syndrome, type 2 diabetes, hypertension, gallbladder disease, certain cancers (colorectal, breast, endometrial), respiratory complications such as obstructive sleep apnea and asthma, as well as osteoarthritis and probably locomotory problems.

Reducing the amount of abdominal visceral AT must be a priority goal of treatment in managing patients with metabolic syndrome. In fact, even a fairly modest decrease in abdominal visceral mass (5-10%) confers a beneficial effect on most of the risk factors for cardiovascular disease and type 2 diabetes, with improvement observed in the lipid profile, insulin sensitivity indices, hypertension and variables associated with an increased risk of thrombosis and inflammation. The pharmacological approach for AT reduction or prevention relies either on anorexigenic drugs acting in the central nervous system, or on drugs which increase energy expenditure by increasing heat production, or which sequester dietary fat in the intestinal lumen. However, current pharmacological approaches have the drawback of causing more or less tolerable side effects.

The need to find effective therapeutic strategies for treating obesity, and in particular abdominal visceral obesity, and/or its consequences, is therefore of utmost urgency worldwide.

Adipocyte differentiation is the process whereby cells progress from the pre-adipocyte stage to adipocytes. Said differentiation occurs in three steps: hyperplasia of pre-adipocytes (the only cells which multiply), differentiation of pre-adipocytes to adipocytes, and lastly, accumulation of triglycerides in mature adipocytes during the process of hypertrophy. Thus, adipose mass in adults increases mainly by hypertrophy of adipocytes, and more rarely by hyperplasia. As a general rule, adipocyte differentiation is usually subject to both positive and negative regulation by factors present in the cell medium, such as hormones, cytokines (or adipokines), growth factors, vitamins, and the like. Some authors have suggested a role of arachidonic acid metabolites, produced in the cyclooxygenase and lipoxygenase pathway, in adipocyte differentiation (Shillabeer G et al., 1998). Furthermore, adipocyte differentiation is regulated in a coordinated manner by a network of transcription factors. It is initiated by exit from the cell cycle and activation of C/EBPα, C/EBPδ (CCAAT/Enhancer-Binding Protein) and SREBP-1, factors which induce the expression of the PPARγ (Peroxisome Proliferator-Activated Receptors gamma) nuclear receptor (Fajas L et al., 1998).

Lipoxygenases are enzymes found in plants and animals which catalyze the oxidation of polyunsaturated fatty acids, including those found in lipoproteins, to hydroperoxy derivatives (Kuhn H and Borngraber S, 1999). In humans there are six genes coding for lipoxygenases: e-LOX-3 (Epidermis-type lipoxygenase 3), 5-LO (5-lipoxygenase), 12-LO (12-lipoxygenase), 12(R)-LOX (12(R)-lipoxygenase), 15-LO-1 (reticulocyte type—15-lipoxygenase-1) and 15-LO-2 (15-lipoxygenase-2). These different lipoxygenases are named according to the specificity of the position of oxidation on arachidonic acid. 12-LO and 15-LO respectively convert arachidonic acid to 12(S)-hydroxyperoxy-5,8,10,14(Z,Z,E,Z)eicosatetraenoic acid (12(S)-HPETE) and 15(S)-hydroxyperoxy-5,8,10,14(Z,Z,E,Z)eicosatetraenoic acid (15(S)-HPETE). Biochemical reduction of 12(S)-HPETE and 15(S)-HPETE respectively leads to the formation of 12(S)-HETE (12-(S)-hydroxy-eicosatetraenoic acid) and 15(S)-HETE (15-(S)-hydroxy-eicosatetraenoic acid) which is the precursor of a class of compounds known as lipoxins (Kuhn H and Borngraber S, 1999). While arachidonic acid is the sole substrate of 15-LO-2 (Brash A R et al., 1997), 15-LO-1 also metabolizes, in a preferential manner, linoleic acid to 13(S)- hydroxyperoxy-9Z,11E-octodecadienoic acid (13(S)-HODE) (Hsi L C et al., 2002). Some lipoxygenases can also produce a mixture of products the relative proportions of which vary according to species. For instance, human 15-LO-1 produces small quantities of 12(S)-HETE (5-10% of final product), in addition to 15(S)-HETE. In mice, 12/15-LO converts arachidonic acid to 12(S)-HETE and 15(S)-HETE in a proportion of 3:1 (Kuhn H and Borngraber S, 1999). The same is true for 12-LO from rats (Watanabe T et al., 1993). In light of the biochemical properties of mouse 12/15-LO and rat 12-LO, these enzymes are generally thought to be the functional equivalents of human 15-LO-1 (hereinafter in the text mouse 12/15-LO and rat 12-LO will be referred to as 12/15-LO).

In addition to their substrate specificity, human 15-LO-1 and 15-LO-2 also differ in terms of their tissue distribution. 15-LO-1 is constitutively expressed in many cell and tissue types with the highest expression in reticulocytes, eosinophils, alveolar macrophages and tracheobronchial epithelium. 15-LO-1 has also been detected in polynuclear leukocytes, inflamed tissues, keratinocytes, corneal epithelial cells, vascular endothelial cells, uterus, placenta, and different cell types of the male reproductive system (Kuhn H and Borngraber S, 1999). 15-LO-2 has a more limited tissue distribution with transcripts found only in prostate, lung, skin, cornea and macrophages (Brash A R, Boeglin W E and Chang M S, 1997) (Rydberg E K et al., 2004).

15-lipoxygenase has previously been implicated in several pathologies including atherosclerosis (Harats D et al., 2000), asthma (Shannon V R et al., 1993), cancer (Shureiqi I et al., 2000, Shureiqi I et al., 2000), glomerulonephritis (Montero A and Badr K F, 2000) and osteoporosis (WO03/066048). The use of 15-LO inhibitors has previously been described for the treatment of many pathologies, for example in patents US2005070589, US2005070588 and US2005065198 for the treatment of atherosclerosis, certain cancers or inflammatory diseases.

The inventors have detected very high levels of transcription of 15-lipoxygenase-1 (15-LO-1) in abdominal visceral AT as compared to abdominal subcutaneous AT. The work carried out by the inventors has revealed the potential role of 15-lipoxygenase in the development of obesity and more particularly in adipocyte differentiation and in the development of abdominal visceral obesity. Inhibitors of 15-LO therefore represent an advantageous therapeutic tool in the treatment of obesity and/or its consequences.

Thus the present invention concerns the treatment of obesity, in particular abdominal visceral obesity, and/or its consequences. More specifically, the application concerns the use of 15-lipoxygenase (LO) inhibitors for preparing medicines useful in the treatment of obesity and/or at least one of its consequences.

SUMMARY OF THE INVENTION

One object of the invention concerns the use of at least one agent partially or totally inhibiting the expression and/or the activity of 15-LO for preparing a pharmaceutical composition intended for treating obesity and/or at least one of its consequences.

Another object of the invention relates to a pharmaceutical composition comprising, in a pharmaceutically acceptable support, at least one agent partially or totally inhibiting the expression and/or the activity of 15-LO optionally in association with one or more therapeutic and/or cosmetic active ingredients.

DETAILED DESCRIPTION OF THE INVENTION

The inventors in the present application have demonstrated the role of 15-LO in the development of obesity, and more particularly in adipocyte differentiation and in the development of abdominal visceral obesity.

One object of the invention therefore concerns the use of at least one agent partially or totally inhibiting the expression and/or the activity of 15-LO for preparing a pharmaceutical composition intended for treating obesity, preferably abdominal visceral obesity, and/or at least one of its consequences.

In the spirit of the invention, 15-LO designates 15-LO-1 and/or 15-LO-2, preferably 15-LO-1. According to a preferred embodiment of the invention, said agent partially or totally inhibiting the expression and/or the activity of 15-LO is an agent partially or totally inhibiting the expression and/or the activity of 15-LO-1.

In the context of the invention, obesity is characterized by a waist circumference greater than or equal to 80 cm in women and 94 cm in men and/or by a BMI greater than or equal to 30 kg/m$^2$. A BMI greater than or equal to 27 kg/m$^2$ is the threshold above which there is a sharp rise in cardiovascular risk.

More specifically, the invention has as object the use of at least one agent partially or totally inhibiting the expression and/or the activity of 15-LO for preparing a pharmaceutical composition intended for treating obesity, preferably abdominal visceral obesity.

In the spirit of the invention, "consequences of obesity" shall be understood to mean type 2 diabetes and/or cardiovascular diseases, hypertension, gallbladder diseases, certain cancers (colorectal, breast, endometrial), respiratory complications such as obstructive sleep apnea and asthma, as well as osteoarthritis and locomotory problems.

The agents partially or totally inhibiting the expression and/or the activity of 15-LO may be compounds of different nature, structure and origin, in particular biological compounds, nuclear factors, antibodies, cofactors, synthetic or natural chemical compounds, and the like. They may also be libraries, particularly libraries of chemotherapeutic agents or libraries of proteins, peptides or nucleic acids, and the like.

In the spirit of the invention, inhibition of enzymatic activity refers to a measured activity which is lower, in comparison to a control activity measured in the absence of treatment with the agent inhibiting 15-LO activity. Inhibition of expression, in turn, refers to a measured expression which is lower in comparison to a control expression measured in the absence of treatment with the agent inhibiting 15-LO activity.

In the present invention, inhibition of the expression and/or the activity of 15-LO can be partial or total. Total inhibition of the expression and/or the activity of 15-LO by an inhibitory agent corresponds to an expression and/or an activity of 15-LO at least 80% lower as compared to an expression and/or activity measured in the absence of treatment with the inhibitory agent. Partial inhibition by an inhibitory agent corresponds to less than 80% decrease in the expression and/or activity of 15-LO as compared to an expression and/or activity measured without treatment by the inhibitory agent.

According to a preferred embodiment of the invention, the agent partially or totally inhibiting the expression and/or the activity of 15-LO is a compound which can partially or totally inhibit the activity of 15-LO.

The invention also has as object the use of at least one compound which can partially or totally inhibit the activity of 15-LO for preparing a pharmaceutical composition intended for treating obesity, preferably abdominal visceral obesity, and/or at least one of its consequences. Even more preferably, the invention concerns the use of a compound which can partially or totally inhibit the activity of 15-LO in order to inhibit adipocyte differentiation.

The terms "compounds which can inhibit the activity of 15-LO" and "15-LO inhibitor" preferably designate a compound inhibiting 15-LO with an $IC_{50}$ less than or equal to 1 µM, preferably less than or equal to 100 nM. The $IC_{50}$ is the concentration of the compound under study which decreases the maximum observed enzymatic activity by 50%. The $IC_{50}$ can be determined by standard methods known to those skilled in the art. In particular, a colorimetric assay provides said measurement: a potential 15-LO inhibitor is preincubated with 15-LO for 10 minutes before adding linoleic acid as substrate, then incubated for another 10 minutes. Formation of the product 13(S)-HPODE is quantified by coupling the reduction of the hydroperoxidated lipid to the oxidation of N-benzoyl-leucomethylene blue in the presence of hemin at pH 5. The absorbance of oxidized methylene blue is directly proportional to the amount of 13(S)-HPODE formed by 15-LO (Auerbach B J et al., 1992). Those skilled in the art can envision other assays, in particular assays in which the initial enzymatic reaction is determined by spectrophotometry at 234 nm by measuring the formation of the conjugated diene (Gan Q F et al., 1996) or a calorimetric assay in which the oxidation of Fe2+ coupled to the reduction of the hydroperoxidated lipid in weakly acidic conditions is detected by formation of a chromophore with xylenol orange which shows strong absorbance at 560 nm (Jiang Z Y et al., 1992).

Preferably, the compounds used in the invention are those which partially or totally inhibit 15-LO activity in a selective manner. The term "selective manner" designates a compound which inhibits 15-LO activity with an $IC_{50}$ which is at least 5 times lower, preferably at least 10 times and more preferably at least 100 times lower, than that observed for other lipoxygenases and cyclooxygenases. In the spirit of the invention, the $IC_{50}$ of a selective 15-LO inhibitor can be greater than or equal to 1 µM.

Preferably, the inhibitor of 15-LO is selective and has an $IC_{50}$ less than or equal to 1 µM.

Several known 15-LO inhibitors can be used in the invention. In particular said inhibitors include synthetic organic molecules, plant extracts and other natural products as well as antibodies directed against 15-LO or antisense molecules.

The literature describes many 15-LO inhibitors which have an $IC_{50}$ less than or equal to 1 µM. Examples include the purines described in (Brathe A et al., 2005), the indolizines described in (Gundersen L et al., 2003) and (Teklu S et al., 2005), the terpenoids described in (Carroll J et al., 2001), including jaspaquinol, the inhibitors described in (Comicelli J A and Trivedi B K, 1999) and in (Weinstein D S et al., 2005), anadanthoflavone, aspenone, lupenone, lupeol, alpha-amyrine and aspigenin described in (Gutierrez-Lugo M T et al., 2004), the caffeic acid analogues, RG-6866 and esculetin described in (Gleason M M et al., 1995), the organobromides described in (Segraves E N et al., 2004), the phthalenes described in (Malterud K E et al., 1999), the polymethoxylated flavonoids described in (Malterud K E and Rydland K M, 2000), ebselen, eicosatetranoic acid and 4-nitrocatechol described in (Walther M et al., 1999), the serotoninamides of arachidonic acid described in (Bezuglov V V et al., 1996), the flavonoids described in (Lyckander I M and Malterud K E, 1992) including sinensetin, tetramethylscutellarein and quercetin or butylhydroxyanisole, nitrocatechol, salicyl-hydroxamate, naphthyl-hydroxamate, 5,8,11,14-eicosatetraynoate (ETYA), 8,11,14-eicosatrinoate described in (Kuhn H and Borngraber S, 1999).

The patent literature also describes many 15-LO inhibitors such as fermented *Glycine max* (L.) extract disclosed in EP1512407, the 15-LO inhibitory compounds disclosed in patent document WO01/96336, the compounds of the imidazolyl, pyrazolyl, oxazolyl and thiazolyl type respectively described in US2005070588, US2005070589 and US2005065198 or compounds of the pyrazole type described in WO2004080999, in particular examples 8, 14, 23 and 26.

Preferably, the 15-LO inhibitors used in the scope of the invention have an $IC_{50}$ less than or equal to 1 µM. Particular examples are compounds of the indole and benzimidazole type developed by Warner-Lambert and described in WO01/96299, compounds of the isothiazolone type such as described in WO96/38144 (in particular examples 23, 24, 27 to 30, 33 and 35), analogues of the compound PD148104 developed by Warner-Lambert such as compound UK-399276 ($IC_{50}$=83 nM) and compounds with the code names CP-65005, UK-369997 and UK-370607, compounds of the thiourea and benzamide type such as 3-amino-N-(3,4-dichlorophenyl)-4-methoxy-benzamide ($IC_{50}$=10 nM) described in WO99/32433 and the 280 exemplified compounds with $IC_{50}$≦1 µM, the 15-LO inhibitor compounds described in WO03/066048, in particular 6,11-dihydro-5-thia-11-aza-benzo[a]fluorine ($IC_{50}$=200 nM–compound 2), 3-amino-N-(3,4-dichlorophenyl)-4-methoxybenzamide ($IC_{50}$=10 nM–compound 3), [[[5-(5,6-difluoro-1H-indol-2-yl)-2-methoxyphenyl]amino]sulfonyl]carabamic acid isobutyl ester ($IC_{50}$=14 nM–compound 6), the compounds of the 1,2,4-trisubstituted benzene type developed by Warner-Lambert and described in WO01/96298 including [[[5-(5,6-difluoro-1H-indol-2-yl)-2-methoxyphenyl]amino]sulfonyl] carabamic acid isobutylester ($IC_{50}$=14 nM), compounds of the tetracyclic indole type and benzopyranoindole described in WO97/12613, compounds of the benzimidazole type described in WO97/12615, particularly compounds having an $IC_{50}$≦1 µM such as the compounds in examples 1 to 3, 5 to 9, 15, 17, 19 to 21, 27 and 37, the 15-LO inhibitor compounds derived from N-sulphonyl-aminophenol mentioned in DE4238233, in particular the compound from example 3 ($IC_{50}$=0.5 µM).

Preferably, the inhibitor used in the scope of the application is selective with respect to 15-LO. Thus the invention has as object the use of the following selective inhibitors for preparing a pharmaceutical composition intended for treating obesity, preferably abdominal visceral obesity, and/or at least one of its consequences:

Compound PD146176 (6,11-dihydro-5-thia-11-aza-benzo[a]-fluorene) from Parke-Davis (now Pfizer) described in Bocan T M et al., 1998, in Sendobry S M et al., 1997 and in patents U.S. Pat. No. 3,388,133, WO97/123613 and U.S. Pat. No. 5,972,980 ($IC_{50}$=0.5-0.8 µM)

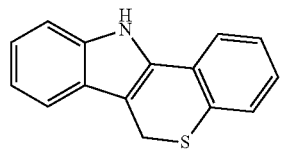

Compounds RP-27493, RP-64835, RP-64407, RP-65208 described in Gleason M M, Rojas C J, Learn K S, Perrone M H and Bilder G E, 1995

Aspigenin described in Gutierrez-Lugo M T, Deschamps J D, Holman T R, Suarez E and Timmermann B N, 2004

Dioxins 4a and 4b described in Segraves E N, Shah R R, Segraves N L, Johnson T A, Whitman S, Sui J K, Kenyon V A, Cichewicz R H, Crews P and Holman T R, 2004

Chomarols A-D, strongylophorin-2 and strongylophorin-3 as well as chromanes No. 25, 26 and 27 described in Cichewicz R H et al., 2004

1-ethoxy-4-cyano-5-ethoxycarbonyl-3H-azuleno[1,2-c]pyran-3-one described in Lin B B and Lin y S, 2004, Lin B B et al., 2004

Compounds 26, 37c, 37f, 37h, 37I, 40a and 40h described in Weinstein D S, Liu W, Gu Z, Langevine C, Ngu K, Fadnis L, Combs D W, Sitkoff D, Ahmad S, Zhuang S, Chen X, Wang F L, Loughney D A, Atwal K S, Zahler R, Macor J E, Madsen C S and Murugesan N, 2005, in particular N-((4-n-pentylbenzene) sulfonyl)-2-(benzofuran-2-yl)tryptamine (compound 37I)

Squalene described in Lin B B and Lin yS, 1992

Trans-phytol described in Lin B B and Lin y S, 1993

Dieranine described in Comicelli J A and Trivedi B K, 1999.

More preferably still, the selective inhibitor used in the scope of the invention is PD146176 or N-((4-n-pentylbenzene)sulfonyl)-2-(benzofuran-2-yl)tryptamine.

Said agents partially or totally inhibiting the activity of 15-LO also include antibodies displaying an affinity for 15-LO, or anti-15-LO antibodies. Preferably, said antibody has a blocking effect and totally or partially inhibits the activity of 15-LO.

Hence the invention concerns the use of at least one antibody partially or totally inhibiting the activity of 15-LO for preparing a pharmaceutical composition intended for treating obesity, preferably abdominal visceral obesity, and/or at least one of its consequences.

The antibodies can be monoclonal or polyclonal antibodies, obtained by any method known to those skilled in the art. Said monoclonal antibodies can be obtained by the classical method of lymphocyte fusion and hybridoma culture or by any other known method of monoclonal antibody preparation. Said polyclonal antibodies can be obtained from serum of an immunized animal, in particular a vertebrate and preferably a mammal with any one of the identified polypeptide sequences or one of the fragments thereof conserving the immunogenicity of the whole protein.

According to another aspect of the invention, the agent partially or totally inhibiting the activity and/or the expression of 15-LO is a compound which can partially or totally inhibit the expression of 15-LO by partially or totally inhibiting the transcription of the gene encoding 15-LO. Thus the invention has as object the use of at least one compound which can partially or totally inhibit the expression of 15-LO for preparing a pharmaceutical composition intended for treating obesity, preferably abdominal visceral obesity, and/or at least one of its consequences.

The different methods of inhibiting gene expression are well known to those skilled in the art. Preferably, the agents partially or totally inhibiting the expression of 15-LO used in the invention are antisense nucleic acids. Antisense therapy generally makes use of a vector, such as a viral vector, which carries the antisense sequence of the mRNA coding for the protein whose expression is to be inhibited, the inhibition then generally being stable since the vector integrates into the genome. It is also possible to use antisense oligonucleotides, which provide transient inhibition of expression. It is also possible to take advantage of ribozyme or RNA interference (siRNA) technology, which prevents a gene from producing a functional protein by destroying the messenger RNA.

Thus, a particular object of the invention relates to the use of at least one agent partially or totally inhibiting the expression and/or the activity of 15-LO in a selective manner for preparing a pharmaceutical composition intended for treating obesity.

Another object of the invention is a pharmaceutical composition comprising, in a pharmaceutically acceptable support, at least one agent partially or totally inhibiting the expression and/or the activity of 15-LO such as described above, optionally in association with one or more other therapeutic and/or cosmetic active ingredients.

Advantageously it is a pharmaceutical composition for treating obesity, preferably abdominal visceral obesity, and/or at least one of its consequences. The pharmaceutical composition according to the invention can also be used to inhibit adipocyte differentiation.

As an example (and not by way of limitation), the other therapeutic and/or cosmetic agents, commercialized or in development, can be selected in the group consisting of:
- anti-diabetics,
- insulin,
- lipid-lowering or cholesterol-lowering molecules,
- antihypertensive agents and hypotensive agents,
- anti-platelet agents,
- anti-obesity agents,
- anti-inflammatory agents,
- antioxidants,
- agents used in the treatment of heart failure,
- agents used for treating coronary failure,
- cancer drugs,
- anti-asthmatics,
- corticosteroids used in the treatment of skin diseases,
- vasodilators and/or anti-ischemic agents.

It is understood that those skilled in the art will make sure to choose said possible other therapeutic agents, and/or the quantity thereof, such that the advantageous properties of the inventive composition are not, or not substantially, altered.

The pharmaceutical compositions according to the invention advantageously comprise one or more pharmaceutically acceptable excipients or vehicles well known to those skilled in the art.

The methods and routes of administration and the doses can be adapted by those skilled in the art according to the patient and the disorder to be treated. The selected dosage strength will depend on various factors including the activity of the particular compound used, the method of administration, the duration of administration, the rate of excretion of the particular compound used, the treatment duration, other drugs, compounds and/or devices used in combination with the particular agent partially or totally inhibiting the expression and/or the activity of the 15-LO, the patient's age, sex, weight, status, general health and medical history and other factors well known in the medical profession. Those skilled in the art can easily determine and prescribe the required quantity of the pharmaceutical composition. For example, the starting doses of the agent partially or totally inhibiting the expression and/or the activity of 15-LO in the pharmaceutical composition can be lower than those required to obtain the desired therapeutic effect and the dosage can be gradually increased until the desired effect is achieved.

The invention also relates to a method for treating obesity, preferably abdominal visceral obesity, comprising administering to a subject, particularly human, an effective amount of at least one compound or one pharmaceutical composition such as defined above. In the spirit of the invention the term "an effective amount" refers to an amount of compound sufficient to produce the desired biological outcome, preferably non-toxic. In the spirit of the invention the term "subject" refers to a mammal and more particularly a human.

The term treatment designates preventive, symptomatic or curative treatment. The agents partially or totally inhibiting the expression and/or the activity of 15-LO used in the invention can be used in humans suffering from a documented disease, comprising the early and/or late stages of the disease. The agents partially or totally inhibiting the expression and/or the activity of 15-LO used in the invention do not necessarily allow the patient with the disease to be cured, but can delay or slow down the progression or prevent further progression of the disease, thereby improving the condition of patients. The agents partially or totally inhibiting the expression and/or the activity of 15-LO used in the invention can also be administered to individuals who are not sick, but who might normally develop the disease, or who have a high risk of developing the disease. The treatment also comprises delaying the development of the disease in an individual who will develop the disease or who is at risk for developing the disease because of age, family history, genetic or chromosomal abnormalities, and/or one or more biological markers of the disease, such as a known genetic mutation, in tissues or fluids. The treatment also comprises administering an agent partially or totally inhibiting the expression and/or the activity of 15-LO used in the invention to individuals who are considered to be predisposed to developing obesity, and preferably abdominal visceral obesity.

Other aspects and advantages of the invention will become apparent in the following examples and appended figures, which are given for purposes of illustration and not by way of limitation.

LEGENDS OF FIGURES

FIG. 1 is a photograph of a gel showing 15-LO-1 expression, determined by RT-PCR, in abdominal subcutaneous and visceral Adipose Tissue (AT) in a group of 10 men.
SC: abdominal subcutaneous AT; V: abdominal visceral AT.

FIG. 2A is a graph of 5-LO, 12-LO and 15-LO-1 expression in abdominal subcutaneous and visceral AT in a group of 83 patients: mean RT-QPCR data.
SC: abdominal subcutaneous AT; V: abdominal visceral AT.

FIG. 2B is a graph comparing relative expression of 5-LO, 12-LO and 15-LO-1 in abdominal subcutaneous and visceral AT in a group of 83 patients: mean RT-QPCR data.
White lines: abdominal subcutaneous AT; black lines: abdominal visceral AT.

Figure 3A:
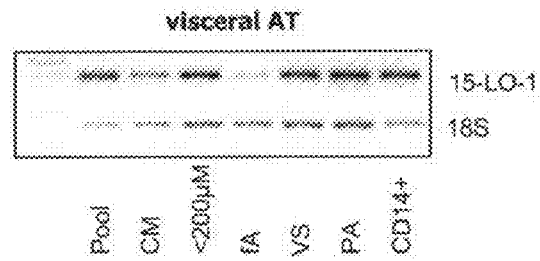

FIG. 3A is a photograph of a gel showing 15-LO-1 expression determined by RT-PCR in fractions of abdominal visceral AT of a patient. PA: pre-adipocyte; fA: mature adipocyte; VS: vascular stroma; CM: cell matrix.

Figure 3B:
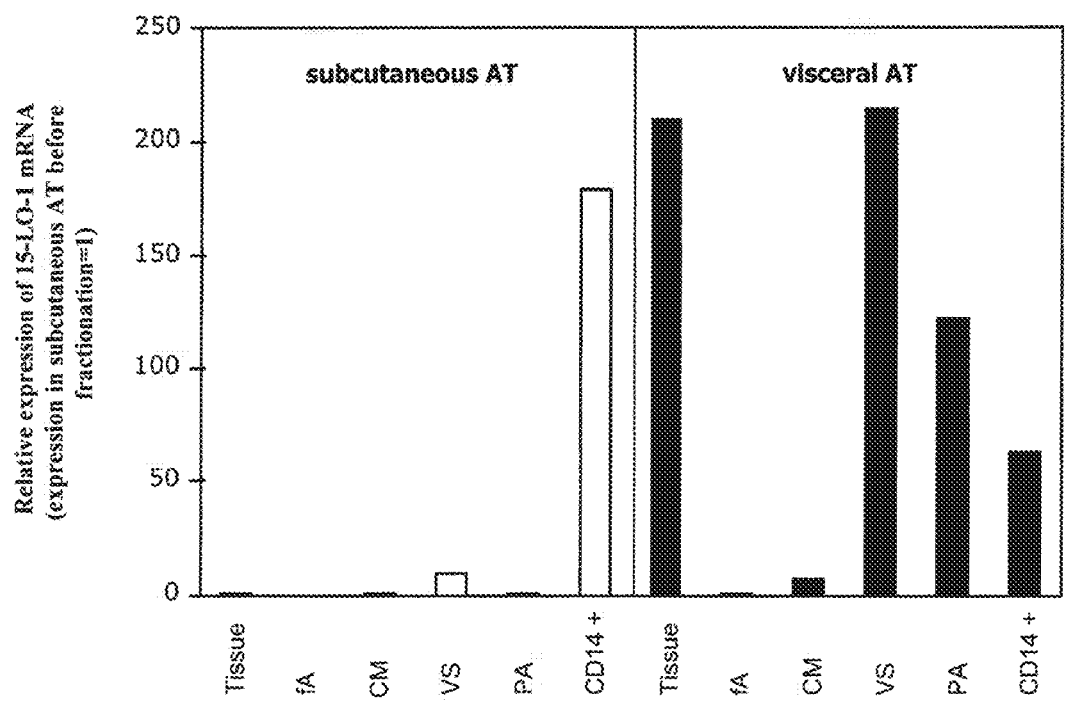

FIG. 3B is a graph of a gel showing 15-LO-1 expression determined by RT-QPCR in AT fractions of a patient.

Figure 4A:
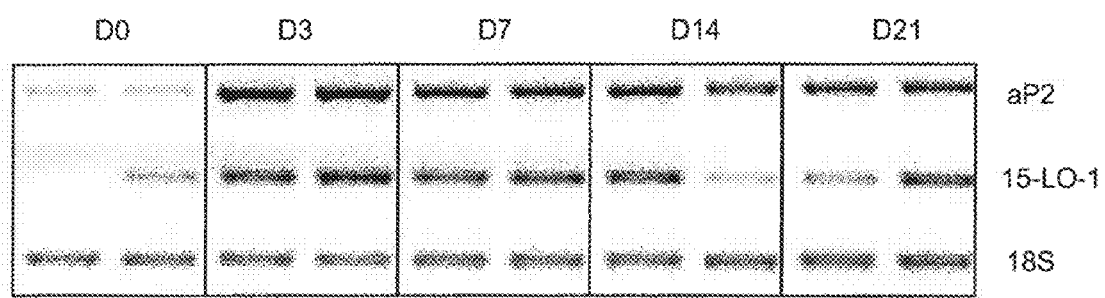

FIG. 4A is a photograph of a gel showing 15-LO-1 expression during differentiation of human visceral pre-adipocytes (PA) from Promocell (PA culture No. 1, passage 4), determined by RT-PCR. D0: confluence; D0-D3: incubation of cells with the differentiation medium; D3-D21: incubation of cells with adipocyte nutritive medium.

Figure 4B:
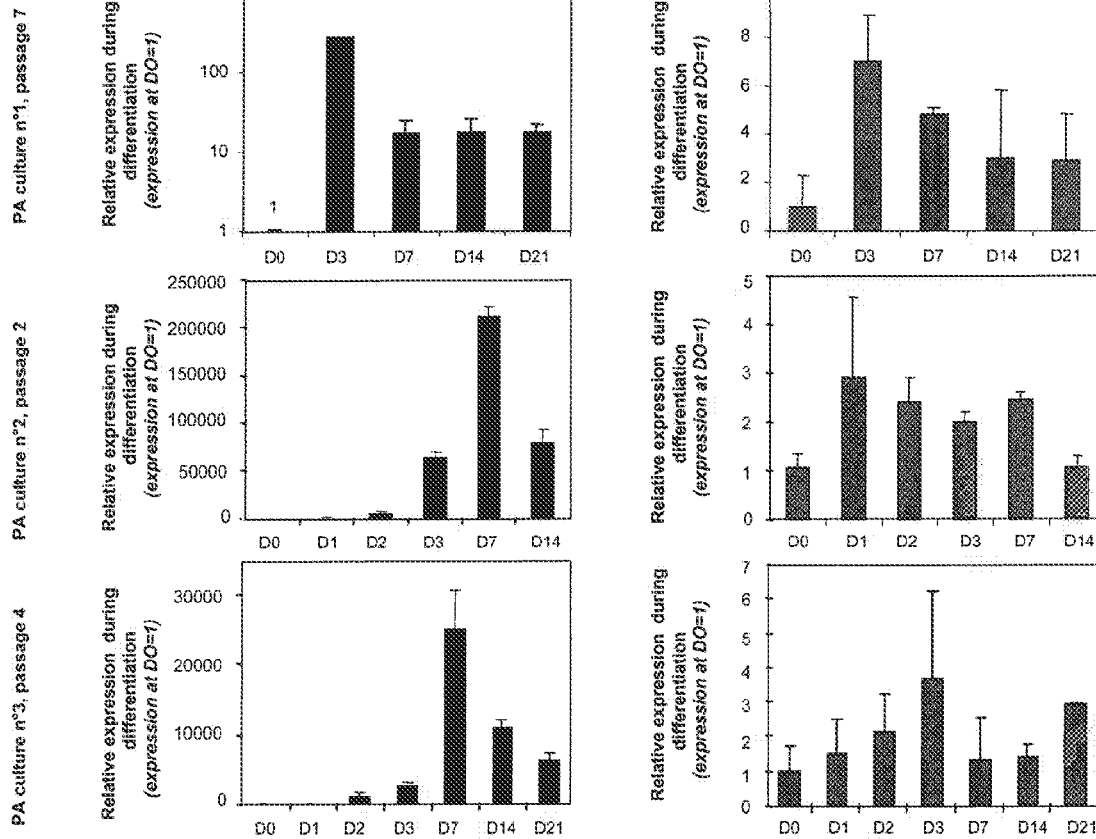

FIG. 4B presents graphs showing 15-LO-1 expression during differentiation of three different human visceral PA cultures from Promocell (PA culture No. 1, passage 7) and Cambrex (PA culture No. 2, passage 2, and PA culture No. 3, passage 4), determined by RT-QPCR.

Figure 5A:
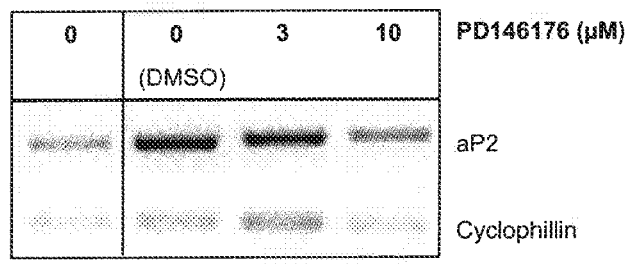

FIG. 5A is a photograph of a gel showing expression of the aP2 marker, determined by RT-PCR, at day 3 of differentiation of a human visceral PA culture (PA culture No. 1, passage 7), in the absence or presence of increasing concentrations of a selective 15-LO inhibitor, PD146176.

Figure 5B:
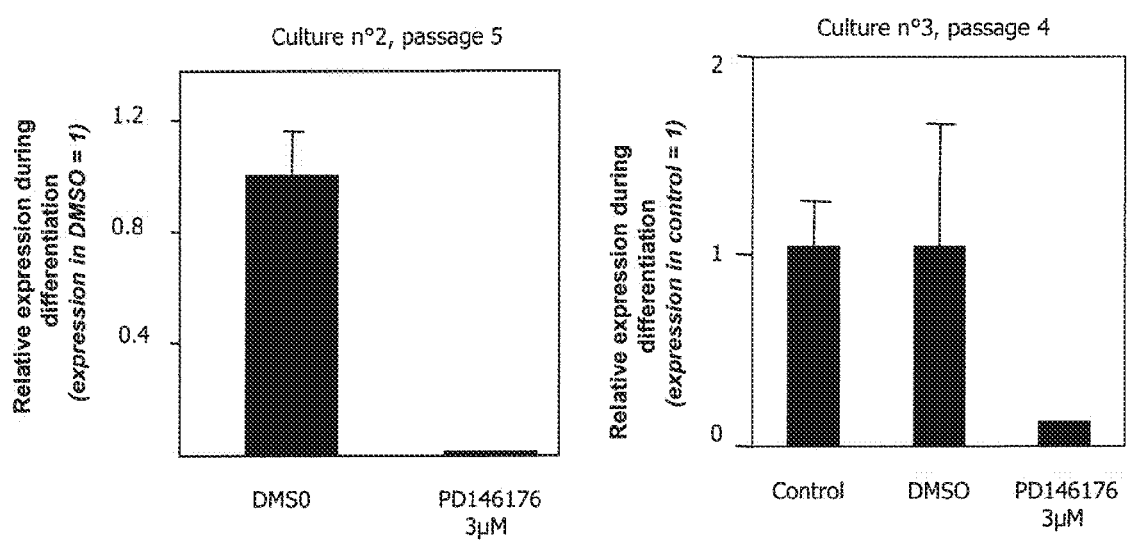

FIG. 5B presents graphs showing expression of the aP2 marker, determined by RT-QPCR, at day 7 of differentiation of two human visceral PA cultures (PA culture No. 2, passage 5 and PA culture No. 3, passage 4), in the absence or presence of increasing concentrations of a selective 15-LO inhibitor, PD146176.

Figure 6A:
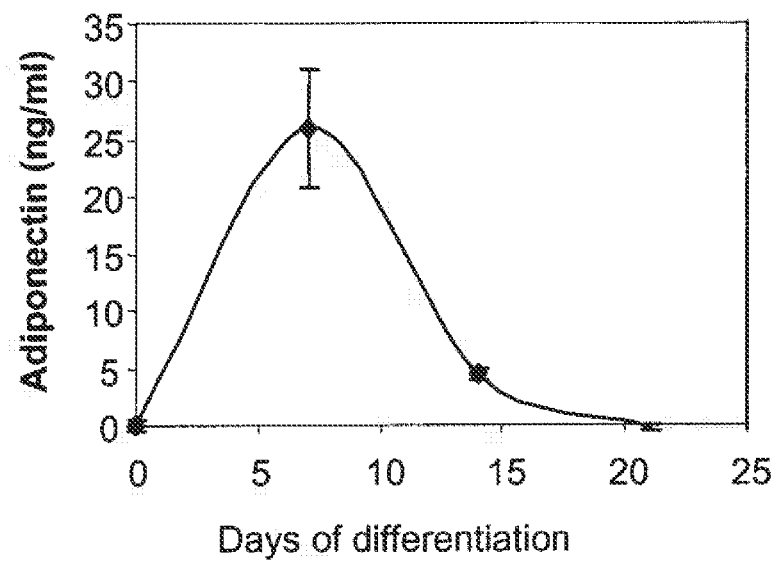

FIG. 6A is a graph showing adiponectin secretion during abdominal visceral PA differentiation (PA culture No. 3, passage 4).

Figure 6B:
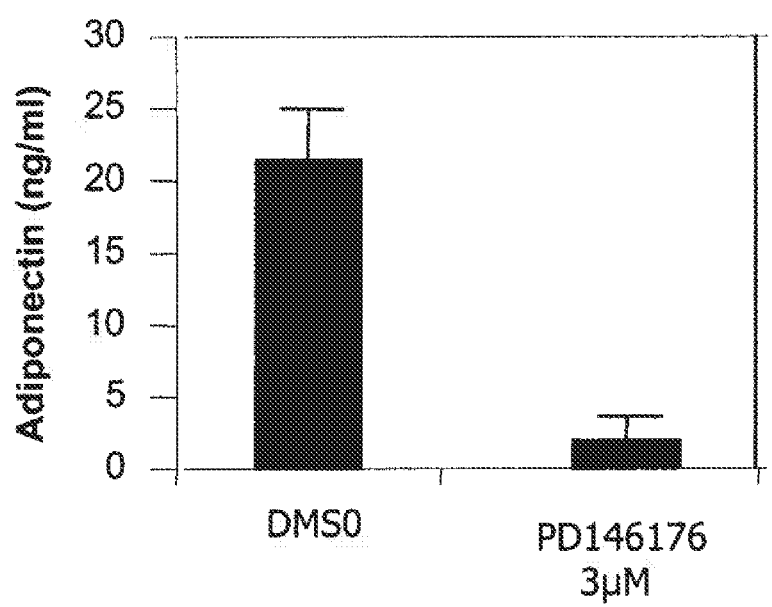

FIG. 6B is a graph showing adiponectin secretion at day 7 of differentiation in the presence of PD146176 (PA culture No. 3, passage 4).

Figure 7A:
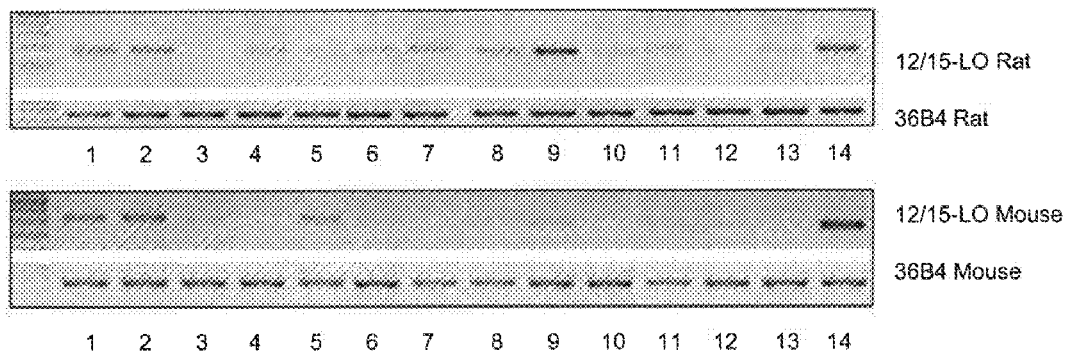

FIG. 7A is a photograph of a gel showing tissue expression of 12/15-LO, the rodent functional equivalent of human 15-LO-1, in the rat and mouse, determined by RT-PCR. 1: perirenal AT; 2: epididymal AT; 3: liver; 4: heart; 5: muscle; 6: kidney; 7: cortex; 8: cerebellum; 9: spleen; 10: testicle; 11 duodenum; 12: jejunum; 13: ileum; 14: lung.

Figure 7B:
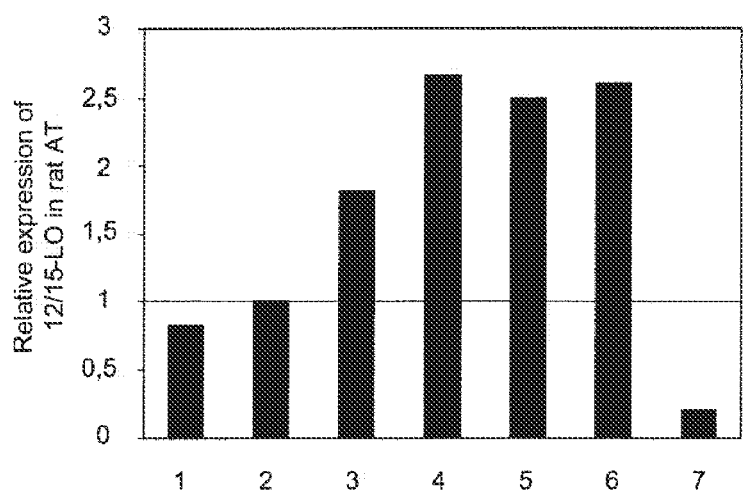

FIG. 7B is a graph showing 12/15-LO expression in different AT deposits in the rat, determined by RT-QPCR. 1: dorsal subcutaneous AT; 2: abdominal subcutaneous AT; 3: omental AT; 4: mesenteric AT; 5: epididymal AT; 6: perirenal AT; 7: interscapular AT.

Figure 8A:
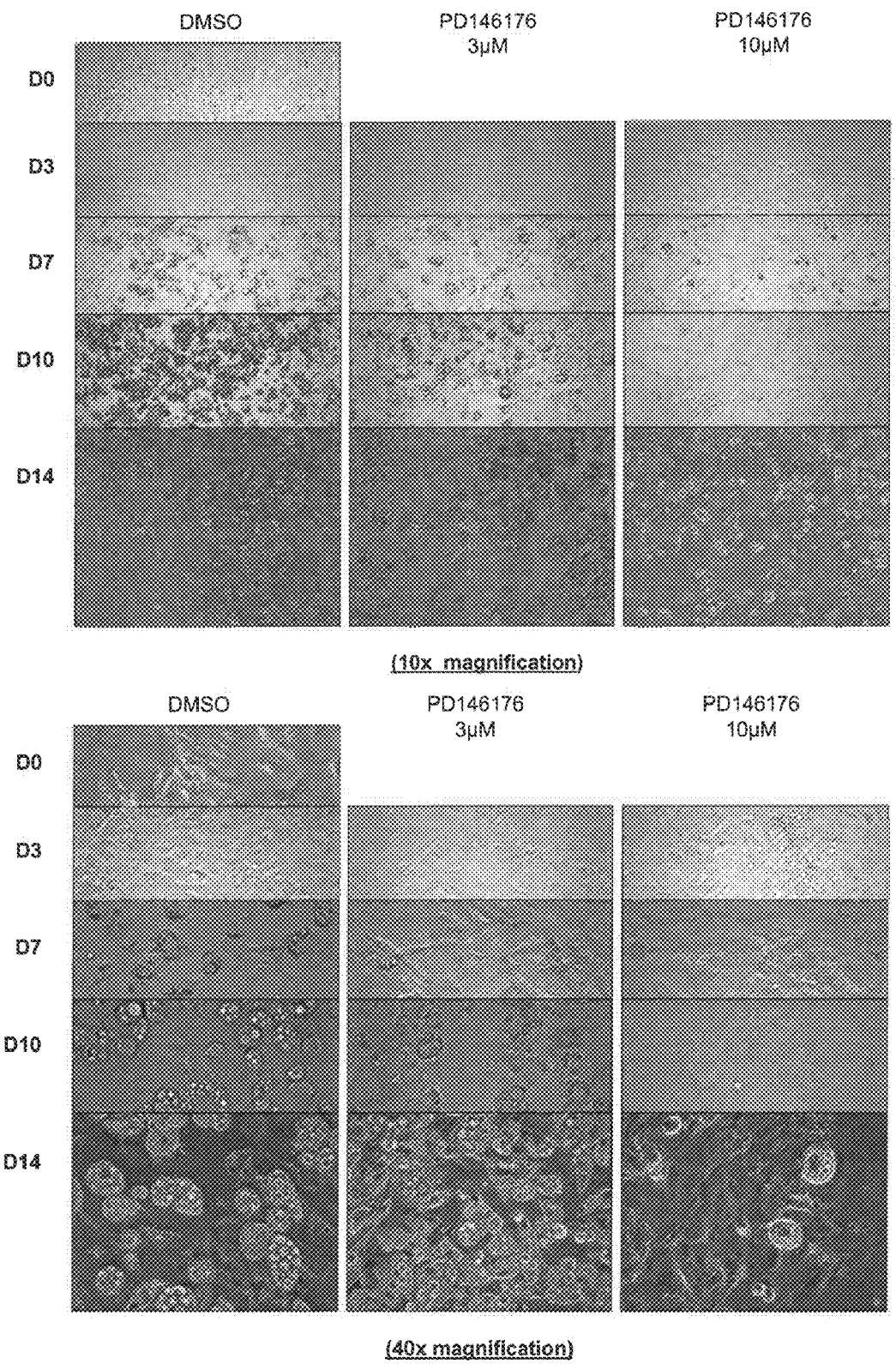

FIG. 8A presents photographs illustrating the effect of PD146176 on the morphology of 3T3-L1 cells during adipocyte differentiation.

Figure 8B:
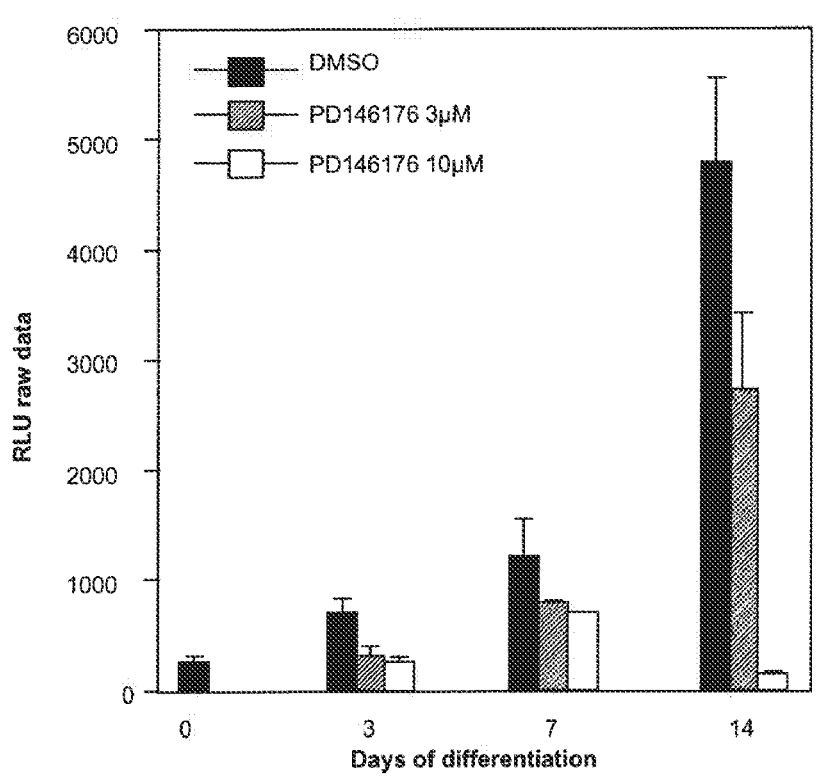

FIG. 8B is a graph showing the effect of PD146176 on lipid accumulation in 3T3-L1 cells during adipocyte differentiation: AdipoRed assay.

Figure 8C:
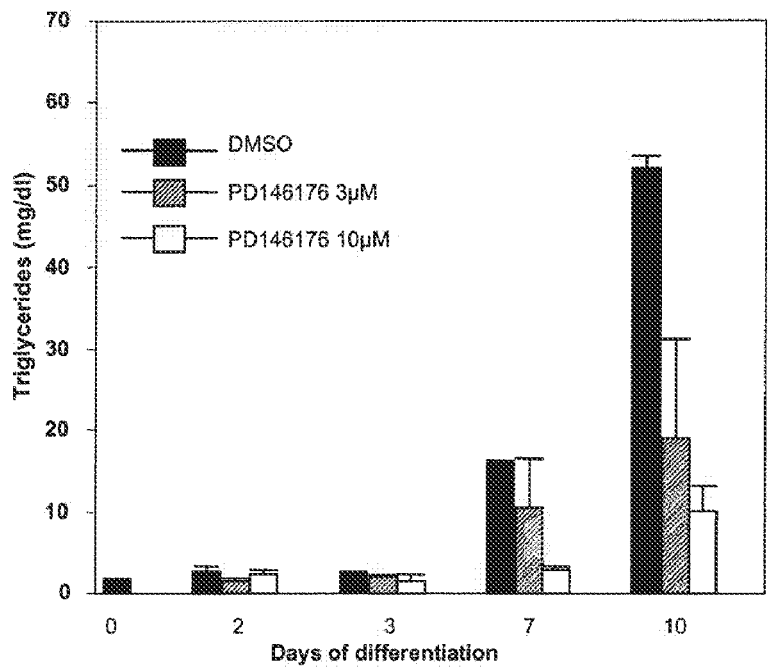

FIG. 8C is a graph showing the effect of PD146176 on triglyceride accumulation in 3T3-L1 cells during adipocyte differentiation.

Figure 8D:
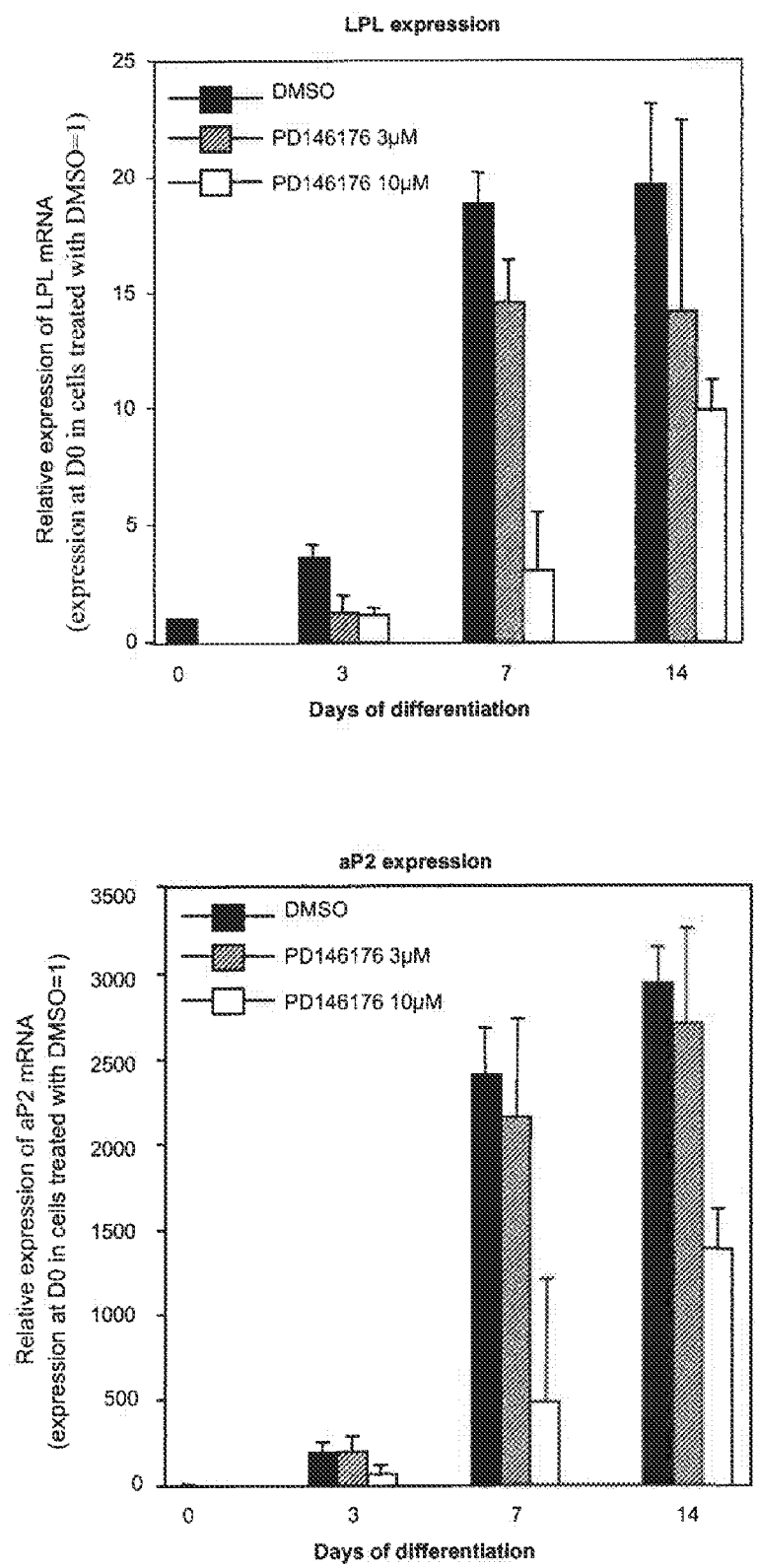

FIG. 8D presents graphs showing the effect of PD146176 on expression of aP2 and LPL (LipoProtein Lipase) by 3T3-L1 cells during adipocyte differentiation.

Figure 9A:
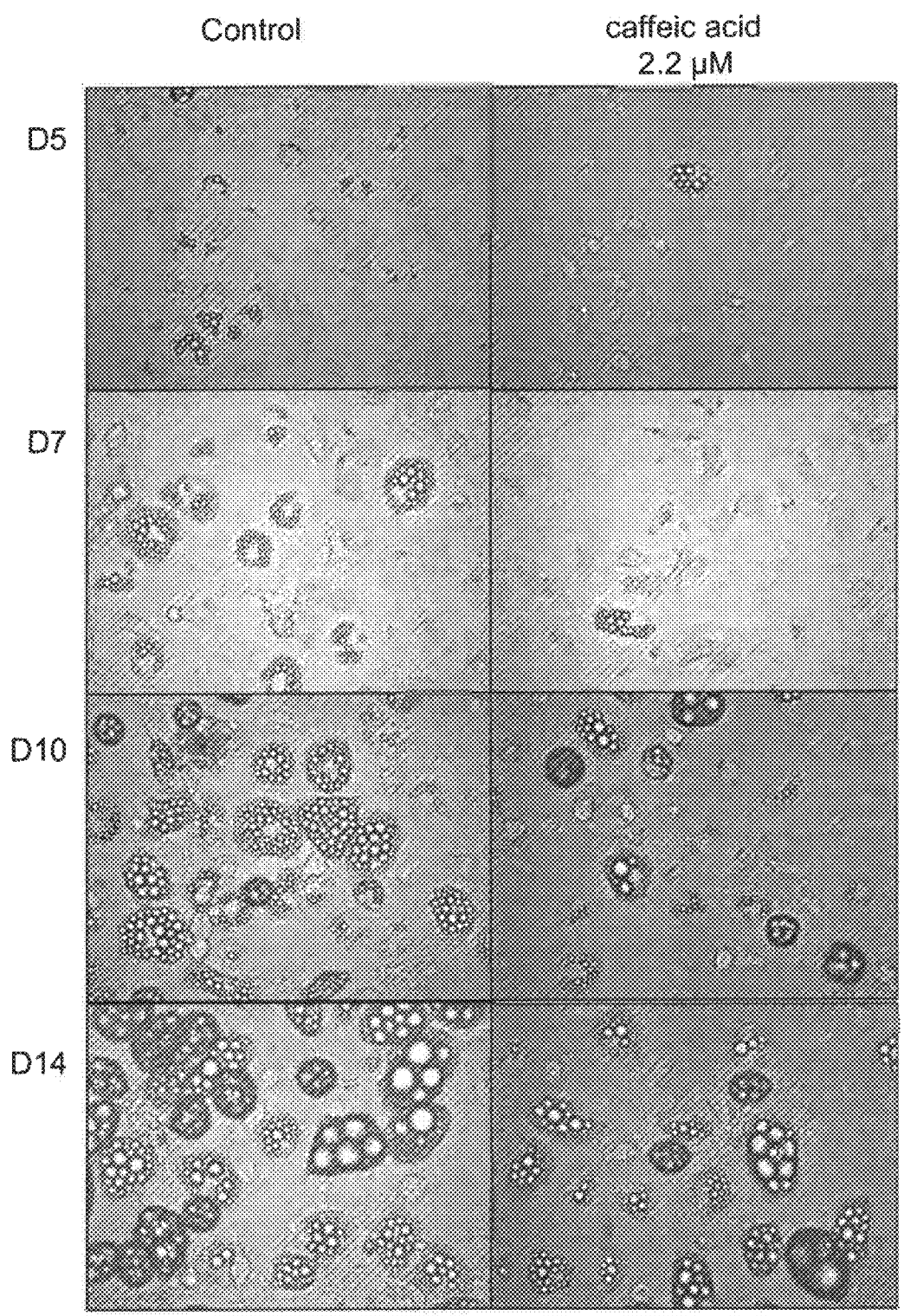

FIG. 9A shows photographs illustrating the effect of caffeic acid on rat PA morphology during adipocyte differentiation.

Figure 9B:
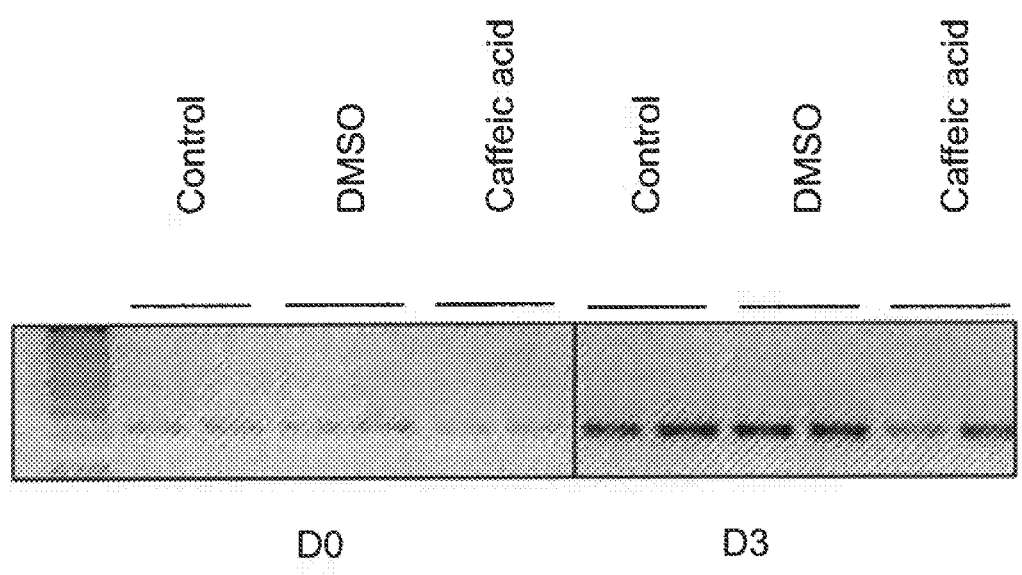

FIG. 9B is a photograph of a gel showing the effect of caffeic acid on aP2 expression by rat PA during adipocyte differentiation.

Figure 10A:
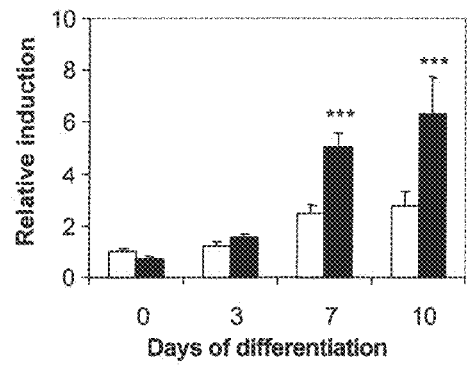

FIG. 10A is a graph showing the effect of overexpression of human 15-LO-1 on intracellular triglyceride accumulation during adipocyte differentiation of 3T3-L1 cells.
White lines: cells transfected with pBlueScript SKII+ plasmid; Black lines: cells transfected with plasmid aP2-15-LO; *** $p<0.001$.

Figure 10B:
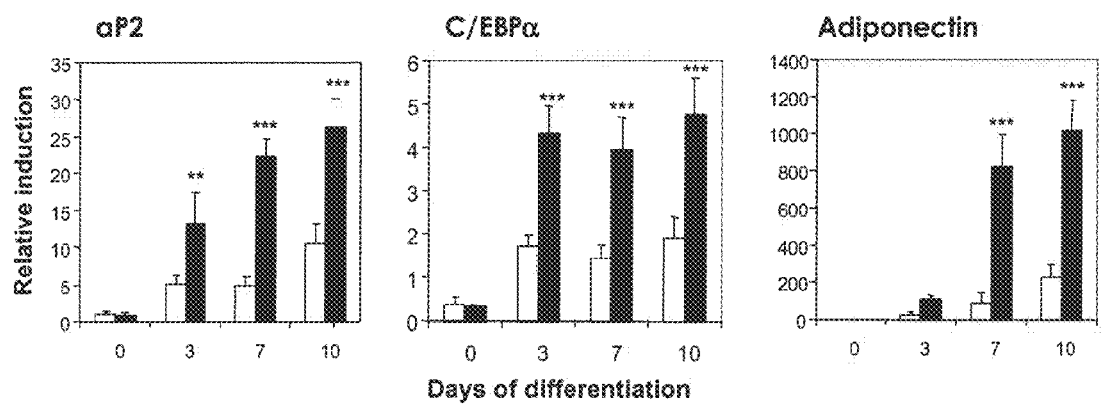

FIG. 10B presents graphs showing the effect of overexpression of human 15-LO on the expression of aP2, C/EBPα and adiponectin during adipocyte differentiation of 3T3-L1 cells.
White lines: cells transfected with pBlueScript SKII+ plasmid; Black lines: cells transfected with plasmid aP2-15-LO;  $p<0.01$; * $p<0.001$.

Figure 10C:
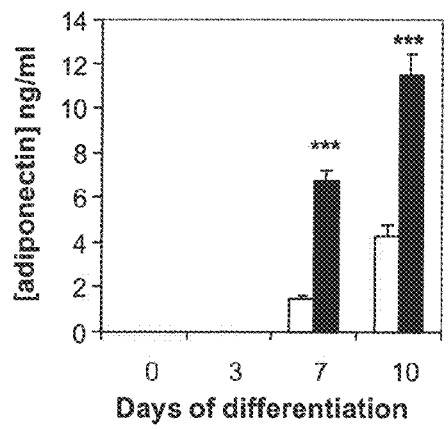

FIG. 10C is a graph showing the effect of overexpression of human 15-LO on adiponectin secretion during adipocyte differentiation of 3T3-L1 cells.
White lines: cells transfected with pBlueScript SKII+ plasmid; Black lines: cells transfected with plasmid aP2-15-LO; *** $p<0.001$.

Figure 11A:
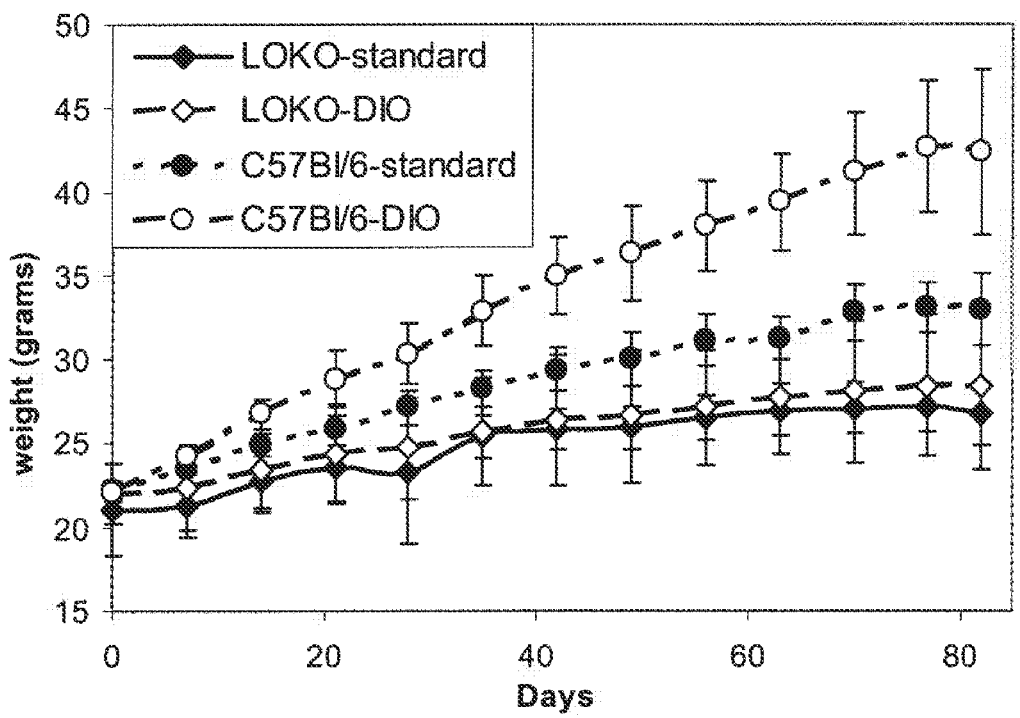

FIG. 11A is a graph showing weight changes in mice deficient for the 12/15-LO gene (named LOKO mice below)

and C57Bl/6j mice on a standard or high fat obesity-inducing diet also called DIO (diet induced obesity).

Figure 11B:
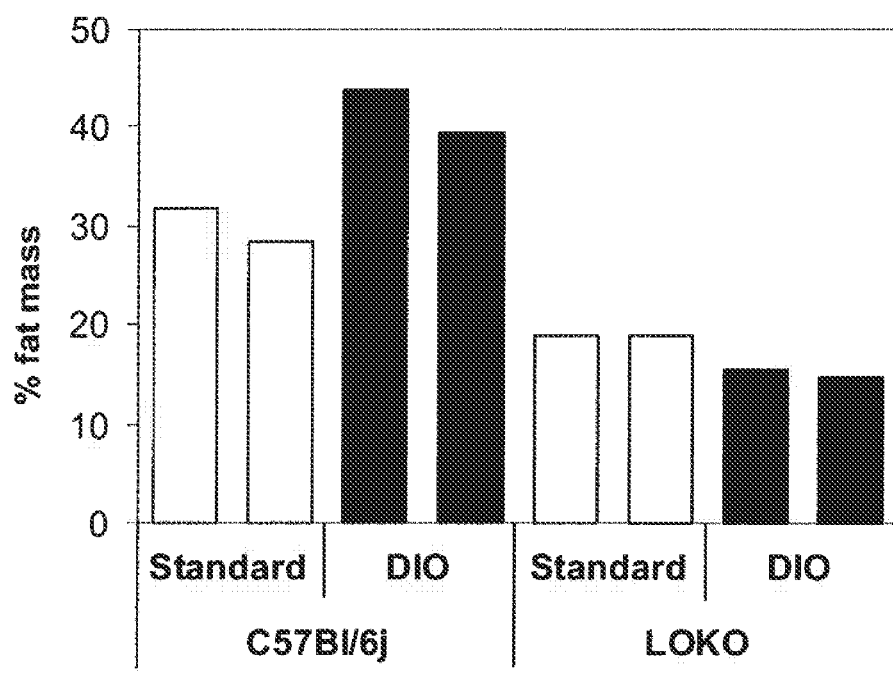

FIG. 11B shows the proportion of adipose mass in LOKO and C57Bl/6j mice fed a standard or high fat diet.

Figure 11C:
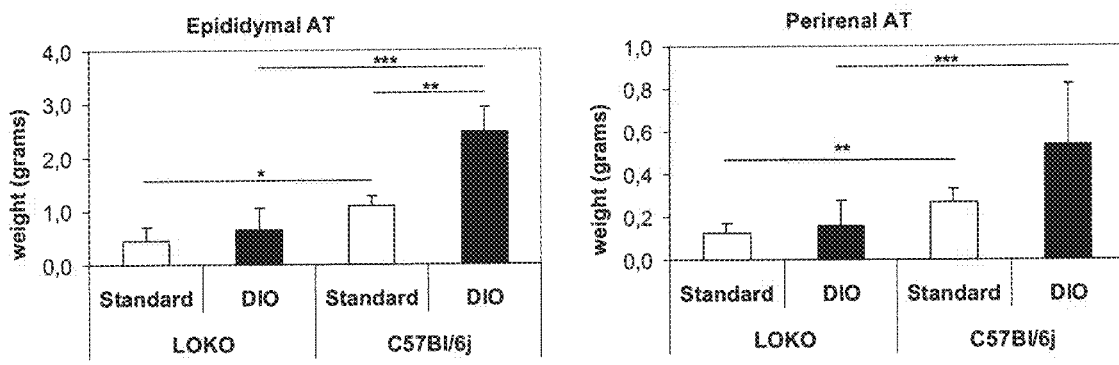

FIG. 11C shows epididymal and perirenal adipose tissue mass in LOKO and C57Bl/6j mice fed a standard or high fat diet.
*p<0.05;  p<0.01,* p<0.001

Figure 11D:
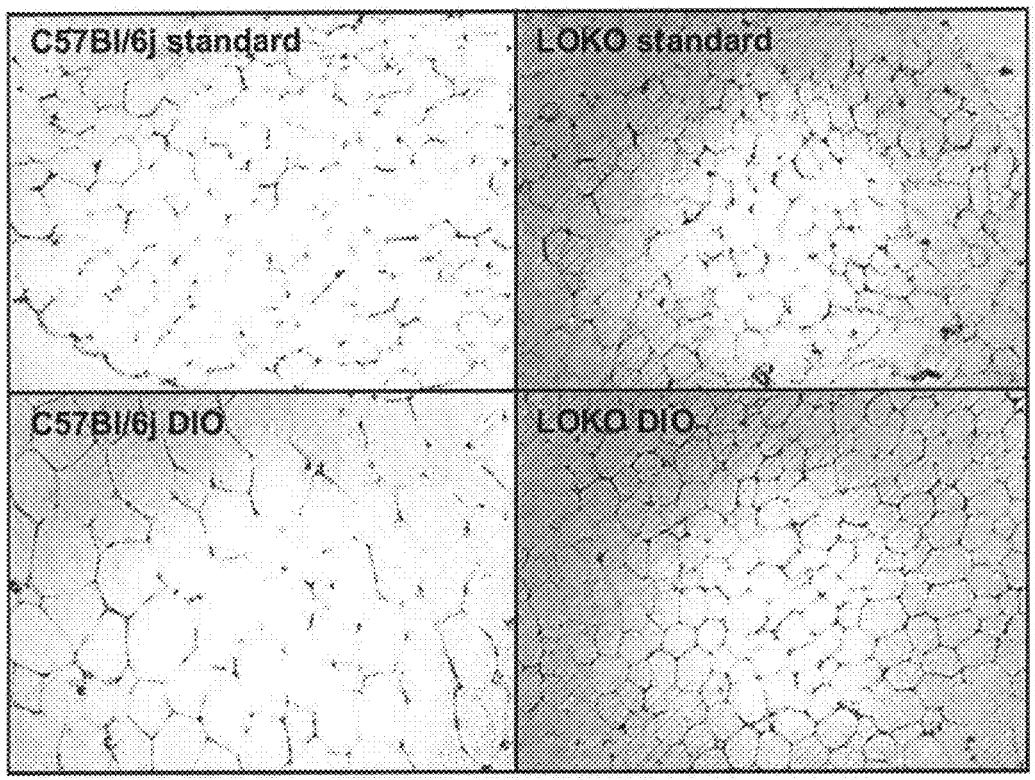

FIG. 11D shows photographs of histological sections of epididymal adipose tissue from LOKO and C57Bl/6j mice fed a standard or high fat diet.

Figure 11E:
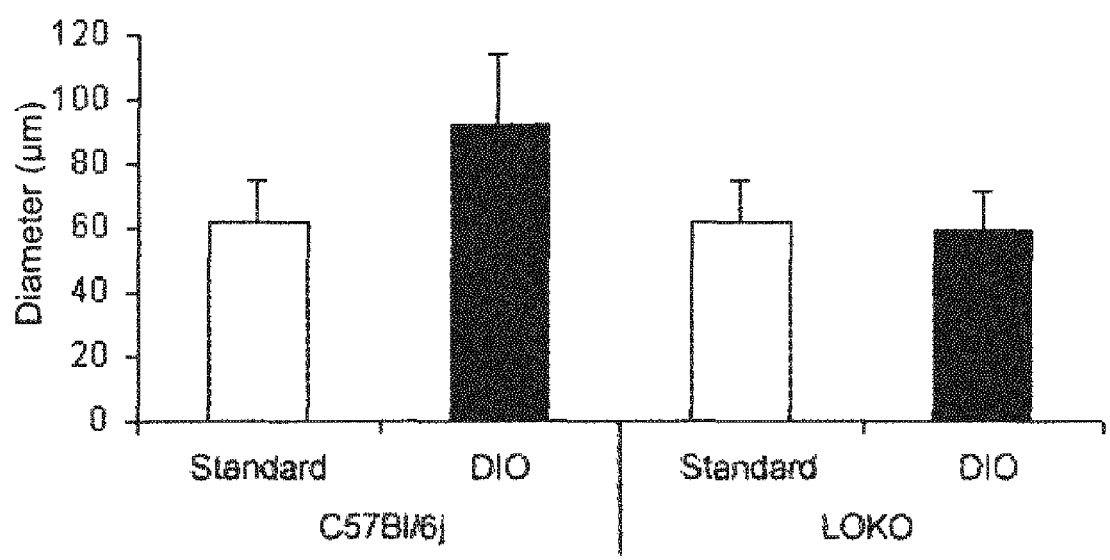

FIG. 11E shows average adipocyte size in epididymal tissue from LOKO and C57Bl/6j mice fed a standard or high fat diet.

EXAMPLES

Example 1

Demonstration of Specific Overexpression of the 15-LO-1 Gene in Human Abdominal Visceral Adipose Tissue (AT) as Compared to Human Abdominal Subcutaneous at in a Group of 10 Men by DNA Chip Technology and by RT-PCR Tissue Harvesting In accordance with the Huriet Law relating to the protection of persons participating in biomedical research, signed informed consent was obtained from each patient before tissues were collected. Demographic and clinical data on the patients were also obtained. For each patient, abdominal visceral AT (omentum) and abdominal subcutaneous AT were harvested during abdominal surgery. Skin and blood vessels were immediately removed from the tissue with surgical scissors and the resulting AT samples were cut into small pieces and immediately frozen in liquid nitrogen.

Extraction of Total RNA from AT

RNA is extracted from AT by the modified guanidium thiocyanate method. Total RNA was treated with DNAse 1 to eliminate any traces of contaminating genomic DNA, then purified on a Quiagen Rneasy column as indicated by the supplier (Qiagen, Courtaboeuf, France).

DNA Chips

DNA chips are prepared so as to compare RNA expression in abdominal visceral AT with RNA expression in abdominal subcutaneous AT from a group of 10 men (see Table 1 for clinical characteristics of the patients).

TABLE 1

| Patient Identification | Age | BMI | Total cholesterol (g/l) | LDL cholesterol (g/l) | HDL cholesterol (g/l) | Total triglycerides (g/l) |
|---|---|---|---|---|---|---|
| 37 | 66 | 28.3 | 1.15 | 0.60 | 0.40 | 0.82 |
| 71 | 58 | 27.0 | 1.80 | 1.13 | 0.36 | 1.56 |
| 90 | 71 | 28.7 | 1.29 | 0.76 | 0.38 | 0.76 |
| 76 | 82 | 27.4 | 0.81 | 0.18 | 0.42 | 1.01 |
| 41 | 85 | 27.0 | 1.04 | 0.61 | 0.19 | 1.18 |
| 29 | 76 | 28.0 | 1.70 | 0.91 | 0.43 | 1.83 |
| 91 | 73 | 28.5 | 1.78 | 1.11 | 0.35 | 1.60 |
| 31 | 64 | 28.1 | 1.49 | 0.91 | 0.29 | 1.41 |
| 21 | 58 | 28.4 | 2.03 | 1.46 | 0.23 | 1.74 |
| 103 | 79 | 27.2 | 1.19 | 0.59 | 0.46 | 0.72 |

Double-stranded complementary DNA (cDNA) are synthesized from 10 μg total RNA using Superscript (SS) II reverse transcriptase, SS choice system buffers (Invitrogen, Cergy Pontoise, France) and oligo-T-7(dt)24 primers (MWG Biotech). Biotinylated complementary RNA (cRNA) are synthesized with the aid of a labelling kit (RNA transcript labelling kit, Enzo, Farmingdale, N.Y.). The DNA chip experiments are carried out on Affymetrix® U133A and U133B chips: hybridization, washing, labelling and scanning are carried out as directed in the Affymetrix® Technical Manual (P/N 700222 rev. 4). Signals are visualized and quantified with Microarray Analysis suite v4 software. The AIC (Akaike Information Criterion) predictive statistical analysis model as well as the BIC (Bayesian Information Criterion) predictive statistical analysis shows a positive correlation between 15-LO-1 expression and abdominal visceral AT.

RT (Reverse Transcription)

1 μg RNA is reverse transcribed by 1 hour incubation at 37° C. with 200 ng random hexanucleotides and 200 units of MMLV enzyme (Sigma) in the presence of 1.5 mM DTT, 187 μM dNTP and 30 units of Rnase inhibitors.

PCR (Polymerase Chain Reaction)

15-LO-1 cDNA is then amplified by PCR using 1 μl of the resulting RT mixtures with 0.3 mM of specific primers (see Table 2 for primers used), 2.5 units of PLATINIUM Pfx DNA polymerase (Invitrogen, 11708-039), 1 mM MgSO$_4$ and 0.3 mM of each dNTP in a final volume of 20 μl. The amplification cycles are 30 sec at 94° C. (denaturation), 30 sec at the specific annealing temperature for each primer pair and 1 min/kb at 68° C. for elongation. The resulting PCR products are analyzed by agarose gel electrophoresis to confirm the presence of a single amplicon of the correct size and sequenced in order to confirm the homology with the amplified gene.

TABLE 2

| Gene | Primer sequences (5' -> 3') | Size of PCR product (bp) | Genbank number |
|---|---|---|---|
| 15-LO-1 | Sense (SEQ ID NO: 1) GGCAAGGAGACAGAACTCAAGGTG Antisense (SEQ ID NO: 2) CTTCAGGCAGGCTCAGGACG | 202 | M23892 |
| Cyclophilin | Sense (SEQ ID NO: 3) GGTGACTTCACACGCCATAATG Antisense (SEQ ID NO: 4) TGTGTTGGGTCCAGCATTTG | 129 | AY739283 |
| 18S | Sense (SEQ ID NO: 5) CGGACACGGACAGGATTGACAG Antisense (SEQ ID NO: 6) AATCTCGGGTGGCTGAACGC | 206 | X03255 |

TABLE 2-continued

| Gene | Primer sequences (5' -> 3') | Size of PCR product (bp) | Genbank number |
|---|---|---|---|
| 36B4 | Sense (SEQ ID NO: 7) CATGCTCAACATCTCCCCCTTCTCC Antisense(SEQ ID NO: 8) GGGAAGGTGTAATCCGTCTCCACAG | 252 | M17885 |

Results

The results of the Affymetrix® chip analysis, presented in Table 3, show that 15-LO-1 is preferentially expressed in abdominal visceral AT as compared with abdominal subcutaneous AT in the 10 male patients, with a ratio of 2.2 and a p value of $7.25 \cdot 10^{-25}$ as determined by the statistical analysis on the Affymetrix® data.

TABLE 3

DNA chip data

| Affymetrix ratio (abdominal visceral AT/abdominal subcutaneous AT) | 2.2 |
| p value | $7.25 \cdot 10^{-25}$ |

Figure 1:
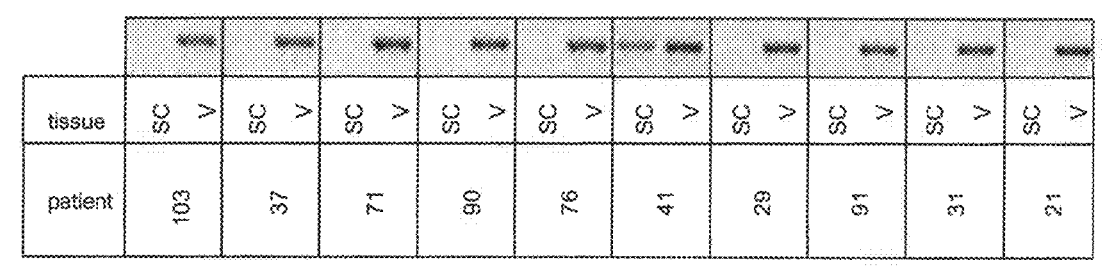

The RT-PCR data shown in FIG. 1 confirm the preferential expression of 15-LO-1 in abdominal visceral AT relative to abdominal subcutaneous AT for each patient studied: in fact, with the exception of patient 41, 15-LO-1 expression is virtually undetectable by classical RT-PCR in abdominal subcutaneous AT whereas an amplicon was seen in the abdominal visceral AT of all the patients.

Example 2

Confirmation of Specific Expression of the 15-LO-1 Gene in Human Abdominal Visceral AT Relative to Human Abdominal Subcutaneous AT, by Quantitative PCR on a Group of 83 Patients, and Selectivity of Said Specific Expression Relative to Other Lipoxygenases Tissue Harvesting and RNA Extraction The results obtained by DNA chip technology were confirmed on abdominal visceral and subcutaneous AT from a group of 83 patients (see Table 4 for clinical data on the patients). Tissues were harvested and RNA extracted as in example 1.

TABLE 4

| Patient Identification | Sex | BMI | Total cholesterol (g/l) | LDL cholesterol (g/l) | HDL cholesterol (g/l) | Total triglycerides (g/l) |
|---|---|---|---|---|---|---|
| 16 | F | 33.3 | 1.43 | 0.71 | 0.42 | 1.41 |
| 17 | F | 17.9 | 2.39 | 1.49 | 0.55 | 1.70 |
| 21 | M | 28.4 | 2.03 | 1.46 | 0.23 | 1.74 |
| 23 | F | 25.5 | 1.45 | 0.89 | 0.27 | 1.42 |
| 24 | F | 25.2 | 2.60 | 1.51 | 0.58 | 2.57 |
| 25 | F | 21.9 | 1.57 | 1.00 | 0.20 | 1.86 |
| 31 | M | 28.1 | 1.27 | 0.70 | 0.31 | 1.28 |
| 33 | F | 23.9 | 1.56 | 0.82 | 0.60 | 0.69 |
| 36 | F | 20.9 | 0.31 | 0.27 | 0.01 | 0.12 |
| 37 | M | 28.3 | 1.06 | 0.38 | 0.42 | 1.29 |
| 39 | M | 24.9 | 1.13 | 0.50 | 0.40 | 1.15 |
| 40 | M | 20.5 | 0.74 | 0.44 | 0.22 | 0.37 |
| 41 | M | 27.0 | 0.89 | 0.54 | 0.25 | 0.50 |
| 42 | M | 17.8 | 0.47 | 0.36 | 0.03 | 0.45 |
| 43 | M | 21.3 | 1.88 | 0.90 | 0.62 | 1.81 |
| 44 | F | 25.7 | 1.98 | 1.00 | 0.62 | 1.81 |
| 46 | F | 34.0 | 1.34 | 0.72 | 0.06 | 2.78 |
| 47 | F | 30.0 | 1.65 | 1.06 | 0.37 | 1.09 |
| 48 | F | 22.6 | 1.31 | 0.55 | 0.63 | 0.64 |
| 49 | F | 48.0 | | | | |
| 51 | M | 43.7 | 1.52 | 1.17 | 0.35 | 3.27 |
| 54 | F | 49.0 | | | | 1.37 |
| 55 | F | 63.6 | 2.12 | 1.59 | 0.53 | 1.63 |
| 60 | F | 53.0 | | | | 0.58 |
| 62 | H | 55.0 | 1.50 | 0.86 | 0.53 | 0.58 |
| 63 | F | 58.0 | | | | 2.21 |
| 64 | H | 56.0 | | | | 1.49 |
| 65 | H | 58.0 | | | | 1.86 |
| 66 | F | 53.0 | | | | 1.48 |
| 67 | F | 51.0 | | | | 1.32 |
| 68 | F | 47.0 | | | | 2.10 |
| 69 | F | 52.0 | | | | 1.57 |
| 71 | M | 27.0 | 1.80 | 1.06 | 0.36 | 1.90 |
| 73 | M | 23.7 | 1.90 | 1.37 | 0.32 | 1.04 |
| 74 | F | 29.1 | 1.68 | 1.02 | 0.56 | 0.50 |
| 76 | M | 27.4 | 1.33 | 0.51 | 0.40 | 2.04 |
| 77 | F | 32.0 | 1.54 | 0.88 | 0.42 | 1.20 |
| 78 | F | 65.4 | 1.58 | 0.92 | 0.22 | 2.17 |
| 81 | F | 49.0 | 1.51 | 0.68 | 0.53 | 1.52 |
| 82 | M | 32.7 | 1.23 | 0.78 | 0.34 | 0.55 |
| 83 | F | 41.0 | 1.55 | 0.95 | 0.25 | 1.80 |
| 84 | F | 60.0 | 1.56 | 0.75 | 0.58 | 1.15 |
| 85 | M | 50.0 | 1.61 | 1.02 | 0.22 | 1.84 |
| 86 | F | 33.2 | 0.24 | 0.29 | 0.01 | 0.29 |
| 87 | F | 61.0 | 1.33 | 0.71 | 0.23 | 1.97 |
| 88 | F | 46.0 | 1.55 | 0.94 | 0.41 | 1.00 |
| 89 | F | 44.0 | 1.66 | 1.01 | 0.37 | 1.37 |
| 90 | M | 28.7 | 1.29 | 0.76 | 0.38 | 0.76 |
| 91 | M | 28.5 | 1.78 | 1.11 | 0.35 | 1.60 |
| 92 | F | 44.0 | 1.53 | 1.02 | 0.30 | 1.08 |
| 93 | F | 44.0 | 1.29 | 0.63 | 0.27 | 1.94 |
| 94 | F | 52.0 | 1.79 | 1.03 | 0.42 | 1.70 |
| 97 | F | 55.0 | 1.74 | 0.93 | 0.22 | 2.95 |
| 98 | F | 46.0 | 1.34 | 0.67 | 0.33 | 1.69 |
| 99 | H | 72.0 | 1.39 | 0.72 | 0.38 | 1.44 |
| 101 | F | 58.0 | 1.54 | 1.02 | 0.35 | 0.86 |
| 102 | F | 46.0 | 1.97 | 1.29 | 0.43 | 1.23 |
| 103 | M | 27.2 | 1.52 | 0.89 | 0.44 | 0.90 |
| 104 | F | 41.9 | 1.60 | 0.83 | 0.41 | 1.81 |
| 105 | M | 25.7 | 1.47 | 0.60 | 0.39 | 2.43 |
| 106 | M | 50.0 | 1.45 | 0.74 | 0.25 | 2.33 |
| 107 | F | 30.4 | 1.67 | 1.01 | 0.47 | 0.97 |
| 109 | M | 62.0 | 1.21 | 0.77 | 0.24 | 0.95 |
| 110 | F | 49.0 | 1.47 | 0.89 | 0.33 | 1.21 |
| 112 | F | 20.5 | 1.71 | 0.74 | 0.50 | 2.33 |
| 113 | F | 67.0 | | | | |

TABLE 4-continued

| Patient Identification | Sex | BMI | Total cholesterol (g/l) | LDL cholesterol (g/l) | HDL cholesterol (g/l) | Total triglycerides (g/l) |
|---|---|---|---|---|---|---|
| 115 | F | | 1.15 | 0.37 | 0.42 | 1.80 |
| 117 | F | 32.0 | 1.30 | 0.80 | 0.36 | 0.70 |
| 118 | F | | 1.19 | 0.76 | 0.23 | 0.98 |
| 119 | F | 37.9 | 1.63 | 0.97 | 0.48 | 0.87 |
| 121 | H | 33.3 | 1.09 | 0.83 | 0.18 | 0.39 |
| 123 | F | 18.5 | 1.43 | 0.88 | 0.43 | 0.58 |
| 126 | F | 27.6 | | | | |
| 129 | H | 27.5 | 1.96 | 1.32 | 0.46 | 0.93 |
| 133 | F | 19.9 | 1.59 | 0.95 | 0.45 | 0.98 |
| 134 | F | 19.5 | 1.82 | 1.21 | 0.53 | 0.43 |
| 135 | F | 27.6 | | | | |
| 136 | H | 27.7 | | | | |
| 140 | H | 19.7 | 1.10 | 0.92 | 0.06 | 0.57 |
| 141 | F | 17.0 | 1.52 | 0.77 | 0.71 | 0.23 |
| 142 | F | 24.4 | 1.15 | 0.81 | 0.23 | 0.56 |
| 145 | M | 28.4 | 1.33 | 0.78 | 0.24 | 1.57 |
| 146 | M | 25.7 | | | | |

It should be noted that the BMI varied widely in the 83 patients studied (17.9 to 72). According to the invention, obesity is characterized by a BMI greater than or equal to 30 kg/m$^2$ and a sharp increase in cardiovascular risk is observed for BMI greater than or equal to 27 kg/m$^2$.

Quantitative PCR (QPCR)

QPCR are carried out by Sybergreen incorporation according to the supplier's instructions (SyberMix Biorad, Mames la Coquette, France) on an IQ-Cycler (Biorad). For each gene, primer use (see Table 5) was optimized for specificity and efficiency (>90%) by analyzing the standard curves and melting curves obtained on serial dilutions of the RT samples. The RT-PCR products obtained were analyzed by agarose gel electrophoresis to confirm the presence of a single amplicon of the correct size and sequence in order to confirm the homology with the amplified gene. Once the optimizations were completed, QPCR are carried out on 1 μl of RT as described in example 1: relative expression of 5-LO, 12-LO and 15-LO-1 is compared to expression of the cyclophilin gene used as internal control.

TABLE 5

| Gene | Primer sequences (5' -> 3') | Size of PCR product (bp) | Genbank number |
|---|---|---|---|
| 15-LO-1 | Sense (SEQ ID NO: 1) GGCAAGGAGACAGAACTCAAGGTG Antisense (SEQ ID NO: 2) CTTCAGGCAGGCTCAGGACG | 202 | M23892 |
| 5-LO | Sense (SEQ ID NO: 9) GCTCATCTGCGAGTGTGG Antisense (SEQ ID NO: 10) GGAGGCATAGGTCAGGTCC | 102 | NM_000698 |
| 12-LO | Sens (SEQ ID NO: 11) CCTGTCTCCTTCCAGTCC Antisens (SEQ ID NO: 12) TCGTCACATCTTCCTTGGTG | 174 | NM_000697 |
| Cyclophilin | Sense (SEQ ID NO: 3) GGTGACTTCACACGCCATAATG Antisense (SEQ ID NO: 4) TGTGTTGGGTCCAGCATTTG | 129 | AY739283 |

AIC and BIC Analyses

The AIC predictive model as well as the BIC predictive analysis shows a positive correlation between 15-LO-1 expression and abdominal visceral AT (Table 6).

TABLE 6

Correlation to clinical data - results of AIC and BIC analyses.

| Gene | AIC with Cyclo as reference (predictive) | BIG with Cyclo as reference (explanatory) |
|---|---|---|
| 15-LO-1 | Tissue *** | Tissue *** |

*** valeur p < 10$^{-6}$

Results

Figure 2A:
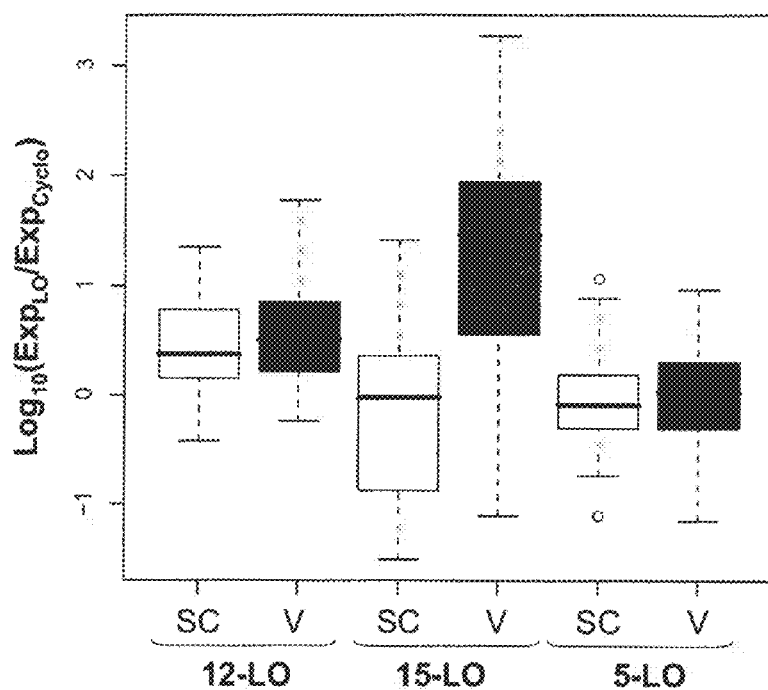
Figure 2B:
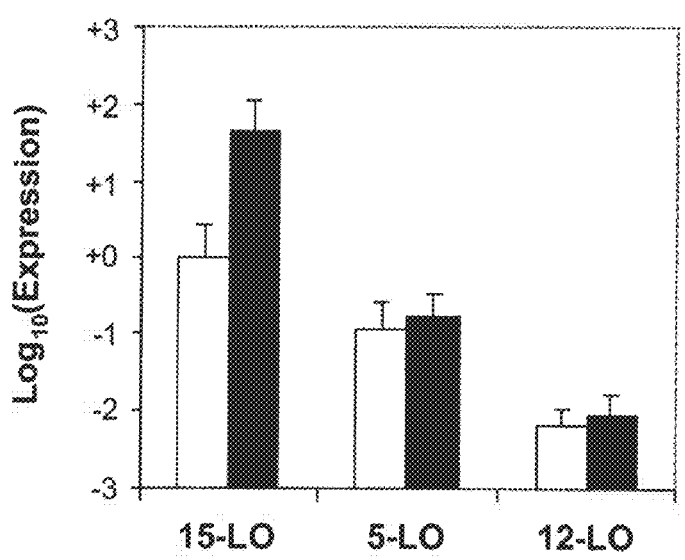

The RT-QPCR data shown in FIG. 2A on RNA from abdominal visceral and subcutaneous AT in 83 patients confirm a preferential expression in abdominal visceral AT. On average, expression levels are 40 times higher in abdominal visceral AT than in abdominal subcutaneous AT. No preferential expression in abdominal visceral versus abdominal subcutaneous AT is seen for 5-LO or 12-LO. Moreover, the RT-QPCR data in FIG. 2B (relative expression normalized to mean 15-LO expression in abdominal subcutaneous AT) indicate that 15-LO is the major form expressed in the patients' AT. For instance, 5-LO is expressed at approximately 12% of the expression level of 15-LO in abdominal subcutaneous AT and 0.4% of the expression level of 15-LO in abdominal visceral AT, whereas 12-LO expression is negligible (<0.4% of 15-LO expression).

Figure 2C:
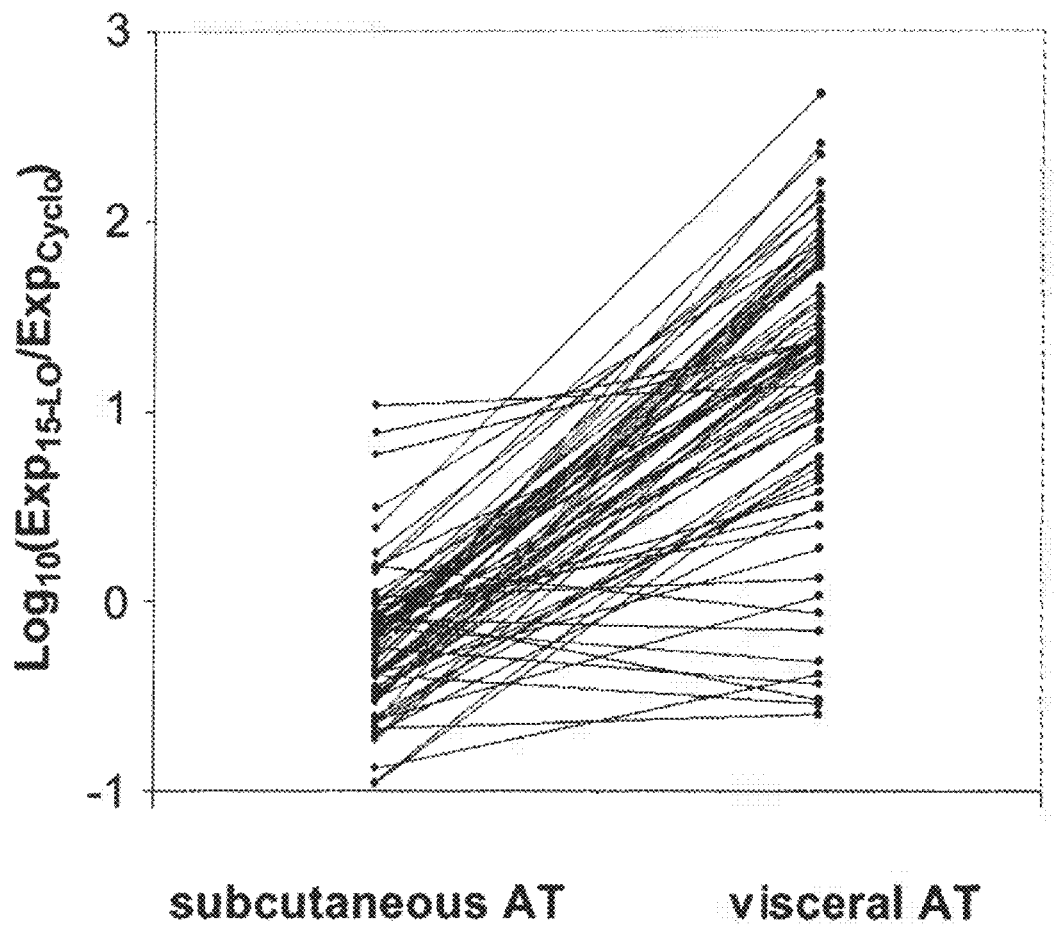
FIG. 2C is a graph of 15-LO-1 expression in abdominal subcutaneous and visceral AT in a group of 83 patients: individual RT-QPCR data.

Analysis of individual data for the 83 patients is shown in FIG. 2C (relative expression normalized to mean expression in abdominal subcutaneous AT from patient No. 17). The results indicate that while basal 15-LO-1 expression in abdominal subcutaneous AT or in abdominal visceral AT is different from one individual to another, a differential expression in abdominal visceral AT versus abdominal subcutaneous AT is observed for the majority of patients. These findings confirm the data obtained on the sample of 10 men.

The QPCR data on a large patient cohort was studied by a stepwise analysis of variance (ANOVA). This method aims to identify the best combination of explanatory variables (clinical factors) which explains the variability seen in the expression data (explained variable). These additional validation studies are carried out on a larger and more heterogeneous patient population consistent with our scientific theme (larger range of BMI, etc.). During the course of the process, the quality of the model is assessed by measuring a score and the process is stopped when the addition or deletion of variables no longer improves the score. Two types of scores are used: AIC score (Akaike Information Criterion) which results in a larger final model given the predictive approach to the data, and BIC score (Bayesian Information Criterion) which provides a simpler final model by virtue of an explanatory approach of the variability contained in the data. Only highly significant variables ($p<10^{-6}$) were considered in the final models proposed by this advanced statistical approach.

The predictive AIC model as well as the predictive BIC model shows a positive correlation between 15-LO-1 expression and abdominal visceral AT.

Together these data show that only 15-LO, the major form in AT, is differentially expressed in abdominal visceral AT, suggesting a specific role of 15-LO in the regionalization of AT in humans, particularly as compared to other lipoxygenases.

Example 3

15-LO-1 Expression is Detected in the Different Fractions of Human AT, Including in Adipocytes and Pre-Adipocytes, and Appears to be the Major Form in the Vascular Stroma Fraction Isolation of Different Human AT Fractions AT are harvested as described in example 1. After removing skin and vasculature, the AT fragments to be used in tissue fractionation are immediately washed in PBS solution supplemented with a penicillin/streptomycin mixture (100 U/100 μg/ml) at 37° C., then incubated in Falcon tubes in digestion buffer (Krebs Ringer buffer 9.5 g/l; 25 mM Hepes; bovine serum albumin 20 mg/ml; 5 mM glucose (Sigma); type 1 collagenase 1.5 mg/ml (Gibco)) with a ratio of AT mass/digestion buffer of 1 g per 10 ml, for 45 minutes at 37° C. with shaking. Digestion lysates are then filtered on a nylon filter (200 μm pore size) to remove any remaining undigested tissue (=matrix or CM). The resulting cell suspension is centrifuged for 15 minutes at 800 g to separate floating adipocytes (fA) which were recovered in the supernatant of the Vascular Stroma (VS) fraction located in the pellet. In order to eliminate red blood cells from the VS fraction, the pellet was suspended in 5 ml of erythrocyte lysis buffer (131 nM $NH_4Cl$ (Carlo Erba); 9 mM $NH_4CO_3$ (Prolabo Rectapur)) and incubated for 15 minutes on ice in this solution. The cell suspension is then centrifuged for 10 minutes at 800 g and the pellet suspended in PBS solution supplemented with a penicillin/streptomycin mixture (100 U/100 μg/ml). Some of said suspension is collected in order to extract RNA (RNA from VS fraction), while another portion of the suspension is incubated on ice for 15-30 minutes with CD14 magnetic microbeads (CD14 MicroBeads, non-human primate: Microbeads conjugated to anti-human CD14 IgG2a monoclonal antibody). The cell suspension is then loaded on a MACS® column to collect CD14+ cells corresponding to the monocyte/macrophage fraction of AT, by using a MACS Separator magnetic column. CD14+ magnetically retained on the column are then eluted according to the supplier's protocol (MACS, Miltenyi Biotec, Paris, France). The cellular fraction which is not held back on the column is depleted of CD14+ cells and enriched in pre-adipocytes and other cell types and was considered as the pre-adipocyte (PA)-enriched fraction.

Extraction of Total RNA from Tissue Fractions and Cells

Total RNA are extracted from the different fractions (CM, fA, VS, CD14+, PA) by direct homogenization in Trizol according to the supplier's instructions (Gibco BRL, Life Technologies), then treated with DNAse I and purified on a Quiagen column by the Quiagen Rneasy procedure.

Analysis of 15-LO-1 Expression by RT-PCR and RT-QPCR

The relative expression of 15-LO-1 is analyzed by the methods described in examples 1 and 2.

Results

The analysis of 15-LO-1 expression data from one patient, shown in FIG. 3A, indicates that 15-LO-1 expression is found in the abdominal visceral AT pool and that said expression is detected in all abdominal visceral AT fractions, with a higher expression in the Vascular Stroma (VS) fraction, which contains PA and CD4+ cells (macrophages), and a lower expression in mature adipocytes (fA).

These data are confirmed by analyzing 15-LO-1 expression by RT-QPCR on the AT fractions from three patients (results shown in FIG. 3B).

Example 4

15-LO-1 Expression is Modulated During Differentiation of Human Visceral PA to Mature Adipocytes Differentiation of Human Abdominal Visceral PA to Adipocytes Human abdominal visceral PA are obtained from Promocell or Cambrex (Human White pre-adipocytes (HWP), Promocell (Heidelberg, Germany), Cambrex (Paris, France)) and cultured according to the supplier's protocol.

HWP from Promocell are maintained in PA growth medium (0.4% ECGS/H, 5% FCS, 10 ng/ml EGF, 1 μg/ml hydrocortisone, 50 ng/ml amphotericin B, 50 μg/ml gentamycin) until confluence. When cells reach confluence, they are differentiated for 3 days in PA differentiation medium (8 μg/ml d-biotin, 0.5 μg/ml recombinant human insulin, 400 ng/ml dexamethasone, 44 μg/ml IBMX, 9 ng/ml L-thyroxin, 3 μg/ml ciglitazone, 50 ng/ml amphotericin B, 50 ng/ml gentamycin), then cultured to the terminal differentiation stage in adipocyte nutritive medium (3% FCS, 8 μg/ml d-biotin, 0.5 μg/ml recombinant human insulin, 400 ng/ml dexamethasone, 50 ng/ml amphotericin B, 50 μg/ml gentamycin). PA from Cambrex are maintained in PA growth medium (10% FCS, 100 U/ml penicillin, 100 μg/ml streptomycin) until confluence, then the medium is replaced by differentiation medium (10% FCS, 10 μg/ml recombinant human insulin, 1 μM dexamethasone, 500 μM IBMX, 200 μM indomethacin, 100 U/ml penicillin, 100 μg/ml streptomycin) throughout the differentiation process.

Extraction of RNA and Analysis of 15-LO-1 and aP2 Gene Expression by RT-PCR and RT-QPCR Total RNA is extracted from the cells at different times during differentiation according to the method described in example 3 and 15-LO-1 expression is analyzed by RT-PCR and RT-QPCR according to the methods of examples 1 and 2. The kinetics of aP2 gene expression is used as a positive control of cell differentiation (see Table 7). For RT-QPCR, the relative expressions of 15-LO-1 and aP2 are reported with reference to the day of confluence (D0) and normalized to cyclophilin expression.

TABLE 7

| Gene | Primer sequences (5' -> 3') | Size of PCR product (bp) | Genbank number |
|---|---|---|---|
| aP2 | Sense (SEQ ID NO: 13) GGCCAGGAATTTGACGAAGTC Antisense (SEQ ID NO: 14) ACAGAATGTTGTAGAGTTCAATGCGA | 251 | J02874 |

As expected, expression of the aP2 marker (adipocyte lipid binding protein) is very low at D0, sharply increases at D3 until D7-D14, then decreases at D21.

Results

Expression of 15-LO-1 during differentiation of PA from Promocell (PA culture No. 1, passage 4; visceral PA were multiplied until passage 4, then differentiated starting from passage 4) is analyzed by RT-PCR. The results in FIG. 4A show that expression of the aP2 marker (adipocyte lipid binding protein) is very low at D0, sharply increases at D3 until D7-D14, then decreases at D21. While the state of the cells at D0 cannot be compared with the PA fraction isolated from AT, 15-LO-1 expression is nonetheless detected at D0. Expression of 15-LO-1 increases at D3 and then follows the same kinetics as aP2 gene expression, increasing during differentiation up to D14, then decreasing at D21. At the adipocyte stage (D21), 15-LO-1 is still expressed.

Similarly, FIG. 4B shows 15-LO-1 expression during differentiation of three different cultures of human abdominal visceral PA: modulation of 15-LO-1 expression during adipocyte differentiation is observed on three independent cultures from three different patients (visceral PA were differentiated starting from passage 7, 2 or 4 depending on the PA culture). For all three cultures, expression of the aP2 marker gradually increases to high levels during differentiation up to D7, then decreases at D14, D21. 15-LO-1 expression increases during the differentiation process but much less so. The peak of 15-LO-1 expression at D3 is found in two patients. Interestingly, the same expression profile is found in culture No. 1 at passage 4 (FIG. 4A) and at passage 7 (FIG. 4B). At the adipocyte stage, 15-LO-1 is still expressed.

Example 5

PD146176, a Selective 15-LO Inhibitor, Inhibits the Differentiation of Human Visceral PA to Mature Adipocytes Treatment of Cells with PD146176

Human abdominal visceral PA from several donors are differentiated as described in example 4. PD146176 diluted in DMSO is added when the PA reached confluence (D0) and is maintained in the medium during the differentiation of PA to adipocytes. DMSO at 0.1% final concentration is added to the culture medium as negative control.

Extraction of RNA and Analysis of aP2 Gene Expression aP2 (adipocyte lipid-binding protein), like adiponectin, is a marker of adipocyte differentiation. Total RNA is extracted from the cells at different times during differentiation (D3, D7) as described in example 3 and expression of the aP2 marker is analyzed by RT-PCR or RT-QPCR as described in examples 1 and 2. Relative expression is reported with reference to the day of confluence (D0) and normalized to cyclophilin expression.

Results

FIG. 5A presents the RT-PCR analysis of aP2 expression at D3 of differentiation of a PA culture (PA culture No. 1, passage 7). At D0, aP2 expression is very low and then sharply increases at D3 for the DMSO control. Addition of PD146176 at the start of differentiation (D0) decreases the expression of the aP2 marker in a dose-dependent manner.

FIG. 5B presents the RT-QPCR analysis of aP2 expression at D7 of differentiation of two PA cultures (PA culture No. 2, passage 5 and PA culture No. 3, passage 4). Expression of aP2 at D7 of differentiation is set to 1 for cells which receives the DMSO control (culture No. 2) or for cells which receives no treatment (culture No. 3): in cells incubated with 3 μM PD146176 starting from D0, aP2 expression is strongly inhibited as compared to DMSO-treated or untreated cells. For instance, PD146176 inhibits 15-LO-1 expression almost completely in culture No. 2 and by 90% in culture No. 3.

The RT-PCR and RT-QPCR data in FIGS. 5A and 5B indicate that expression of the aP2 marker during differentiation of PA cultures decreases in a dose-dependent manner after addition of PD146176.

Example 6

PD146176, a Selective 15-LO Inhibitor, Decreases Adiponectin Secretion During Differentiation of Human Visceral PA Treatment of PA with PD146176

Human abdominal visceral PA from several donors are differentiated as described in example 4. PA which have reached confluence (D0) are incubated with PD146176 as described in example 5.

Analysis of Adiponectin Secretion

Adiponectin is a factor secreted by adipocytes and, like aP2, serves as a marker of adipocyte differentiation in our cultures. Adiponectin concentrations is determined in culture supernatants at different times during differentiation using the Quantikine human adiponectin/ACRP30 kit according to the supplier's instructions (R&D, Minneapolis, Minn., USA).

Results

FIG. 6A shows that adiponectin secretion in culture supernatants increases during the differentiation of human abdominal visceral PA with a peak of secretion at D7.

In cells treated with PD146176 starting from D0, adiponectin secretion is sharply decreased at D7, as shown in FIG. 6B. This finding confirms the inhibition of differentiation observed by measuring aP2 gene expression at D7 of differentiation (FIG. 5).

Example 7

12/15-LO, the Functional Equivalent of 15-LO-1 in Rodents, is Primarily Expressed in AT of Rat and Mouse, with Higher Expression in Mesenteric, Epididymal and Perirenal AT than in Abdominal Subcutaneous AT Extraction of Rodent Tissues C57BI6 mice and Sprague Dawley rats (Charles River Laboratories) are kepi on a standard day/night cycle and fed ad libitum with rodent feed. Sprague Dawley rats are sacrificed by pentobarbital injection and mice were sacrificed by cervical dislocation after isoflurane anesthesia.

Extraction of AT

The different AT deposits are collected (abdominal subcutaneous AT, dorsal subcutaneous AT, omental AT, mesenteric AT, perirenal AT, epididymal AT and intercapsular AT), cut into small pieces and directly transferred in liquid nitrogen.

RNA Extraction and Analysis of 12/15-LO Expression by RT-PCR and RT-QPCR

Total RNA from non-AT tissues is extracted as described in example 3. Total RNA from AT was extracted as described in example 1. Reverse transcription is carried out as in example 1 and rodent 12/15-LO expression (see Table 8) is analyzed by RT-PCR or RT-QPCR as described in examples 1 and 2.

TABLE 8

| Gene | Primer sequences (5' -> 3') | Size of PCR product (bp) | Genbank number |
| --- | --- | --- | --- |
| r12/15-LO | Sense (SEQ ID NO: 15) GGCTCCAACAACGAGGTCTACCTG Antisense (SEQ ID NO: 16) AACCAGGCGTCATCCGTGAG | 182 | NM_031010 |
| m12/15-LO | Sense (SEQ ID NO: 17) GGCTCCAACAACGAGGTCTACCTG Antisense (SEQ ID NO: 18) GAGAGTCTTCAACCACGGTG | 316 | NM_009660 |

Results

RT-PCR analysis of 12/15-LO tissue expression in the rat and mouse is shown in FIG. 7A. It can be seen that tissue distribution of 12/15-LO is fairly limited in rats and mice: expression is detected in lung, spleen (in the rat), muscle (rat and mouse) and in AT.

Analysis of 12/15-Lox expression in different AT deposits in the rat confirms that the gene is expressed in the different AT deposits, as shown in FIG. 76. Expression arbitrarily set to 1 in dorsal abdominal subcutaneous AT. As in humans, expression is lower in abdominal subcutaneous AT (abdominal and dorsal) as compared with deep AT deposits such as omental AT, mesenteric AT, epididymal AT and perirenal AT. 12/15-LO expression occurrs preferentially in AT since low expression in brown fat (intercapsular AT) is seen in comparison with the other deposits.

Example 8

PD146176, a 15-LO Inhibitor, Inhibits Adipocyte Differentiation in 3T3-L1 Cells 3T3-L1 Cell Culture and Differentiation to Adipocytes The mouse PA 3T3-L1 cell line (ATCC) is maintained in DMEM (Dulbecco's Modified Eagle's minimal essential Medium) supplemented with 10% FCS, L-glutamine and a penicillin/streptomycin mixture. At confluence (D0), 3T3-L1 cells are differentiated by a two-day treatment with a mixture of dexamethasone (0.1 μM), isobutylmethylxanthine (0.25 mM) and insulin (0.4 μM). Cells are then maintained on insulin for another 14 days until differentiation is complete. Photographs are taken at different times after confluence in order to visually follow the differentiation process.

Treatment of Cells with PD146176

PD146176 is added to the 3T3-L1 cells when they reach confluence (D0) and is maintained throughout the differentiation process with replacement every other day at the same time as the insulin.

Quantification of Differentiation with AdipoRed

The gradual accumulation of intracellular droplets is also used as a functional marker of differentiation to adipocytes. To quantify this accumulation the 3T3-L1 cells are differentiated in 96-well microtiter plates. The plates are removed from the incubator on the day of the assay in order to reequilibrate to room temperature. The medium is removed, the cells carefully rinsed with 200 μl PBS, and 200 μl PBS are then added to each well followed by 5 μl AdipoRed reagent (Cambrex, Paris, France). The plates are mixed before measuring fluorescence on a fluorimeter at an excitation wavelength of 485 nm and an emission wavelength of 535 nm.

Assay of Triglycerides

To assay intracellular triglycerides, the 3T3-L1 cells are differentiated in 24-well microtiter plates. Cells are washed three times in PBS, then 500 μl of homogenization buffer (150 mM NaCl, Tris HCL pH 8, 0.1% Triton X-100) are added to each well. The cells are scraped into a tube and lysed by sonication for 10 seconds at 40 watts. The lysate is then filtered on a 0.2 μM millipore filter. The assay is carried out on 125 μl of the resulting lysate using the Triglyceride L-type kit (Wako). The assay is normalized for the protein content of the lysates.

RNA Extraction and Analysis of LPL and aP2 Expression by RT-QPCR

Total RNA is extracted at different times during differentiation as described in example 3 and expression of the aP2 and LPL (lipoprotein lipase) genes is analyzed by RT-QPCR according to the method described in example 2 (see Table 9).

TABLE 9

| Gene | Primer sequences (5' -> 3') | Size of PCR product (bp) | Genbank number |
|---|---|---|---|
| mLPL | Sense (SEQ ID NO: 19) ACTGCCACTTCAACCACAGC Antisense (SEQ ID NO: 20) ACTCCTCCTCCATCCAGTTG | 240 | I 6678709 |
| maP2 | Sense (SEQ ID NO: 21) GTGATGCCTTTGTGGGAACCTG Antisense (SEQ ID NO: 22) TCACCTTCCTGTCGTCTGCG | 240 | NM-024406 |
| m/rCyclophilin | Sense (SEQ ID NO: 23) GGGTGGTGACTTTACACGCC Antisense (SEQ ID NO: 24) GGACAAGATGCCAGGACCTG | 109 | GI6679438 |

Results

The change in 3T3-L1 cell morphology during adipocyte differentiation is illustrated in FIG. 8A. It can be seen that cells start to acquire an adipocyte morphology with lipid-loaded droplets appearing from D7 of differentiation. The addition of PD146176 at D0 induces a dose-dependent inhibition of lipid accumulation in the cells, with the droplets being less numerous and smaller in size.

FIG. 8B shows that AdipoRed staining gradually increases during differentiation to 5000 RLU at D14, which corresponds to lipid loading of the 3T3-L1 cells. The addition of PD146176 at D0 sharply decreases AdipoRed staining in a dose-dependent manner starting from D3 of differentiation. Inhibition is still observed at D7 and is even more pronounced after 14 days of differentiation, where cells treated with 10 µM PD146176 have a level of AdipoRed staining similar to that seen at D0.

FIG. 8C illustrates triglyceride accumulation in 3T3-L1 cells during adipocyte differentiation: the cells gradually become loaded with triglycerides during the differentiation process. This increase follows exactly the same kinetics as the AdipoRed staining (FIG. 8B). The addition of PD146176 at D0 led to a dose-dependent decrease in triglyceride accumulation. For the highest concentration (10 µM), an 80% decrease was observed at D10 relative to the control.

Lastly, FIG. 8D shows that expression of the aP2 and LPM markers gradually increased during differentiation of 3T3-L1 cells and that addition of PD146176 at D0 leads to a dose-dependent decrease in the expression of these two markers starting from D3 of differentiation.

Together these data show that PD146176, an inhibitor of 15-LO, inhibits the differentiation of 3T3-L1 cells to adipocytes. These results therefore indicate that 15-LO is a pro-adipogenic factor and that inhibition of its activity leads to inhibition of adipocyte differentiation.

Example 9

Caffeic Acid Inhibits the Differentiation of Rat Primary PA to Mature Adipocytes Differentiation of Rat PA Cells from the VS fraction (isolated by the same method as that described in example 3) are seeded in 6-well plates at a density of 80,000 cells/cm$^2$ in medium 199 (Gibco) supplemented with 10% FCS and a penicillin/streptomycin mixture. After a 16-hour incubation to allow cell adherence, the wells are gently rinsed with PBS to remove any non-adherent material. The cells are grown to confluence (D0) at which time the medium 199 is removed and replaced by ITT medium (DME/Ham's F12, 15 mM NaHCO$_3$, 15 mM Hepes, 33 µm biotin, 17 µM panthotenate, 0.5 µM human insulin, 0.2 nM triiodothyronine and antibiotics) without addition of serum. Cells are maintained in this medium to enable differentiation; the medium is changed every 2-3 days during the differentiation process.

Treatment of Cells with Caffeic Acid

Caffeic acid (2.2 µM) was added when the rat PA reach confluence (D0) and is maintained during the adipocyte differentiation process. At a concentration of 2.2 µM, caffeic acid is considered as a selective inhibitor of 15-LO (Shureiqi I, Chen D, Lee J J, Yang P, Newman R A, Brenner D E, Lotan R, Fischer S M and Lippman S M, 2000). DMSO is added to 0.1% final concentration to the culture medium as negative control.

RNA Extraction and Analysis of aP2 Gene Expression

Total RNA is extracted at different times during differentiation according to the method described in example 3 and aP2 and LPL gene expression is analyzed by quantitative RT-PCR as described in example 2 (see Table 10).

TABLE 10

| Gene | Primer sequences (5' -> 3') | Size of PCR product (bp) | Genbank number |
|---|---|---|---|
| raP2 | Sense (SEQ ID NO: 25) AACTCGTCTCCAGTGAGAAC Antisense (SEQ ID NO: 26) ATGCTCTTCACTTTCCTGTC | 223 | U75581 |
| m/rCyclophilin | Sense (SEQ ID NO: 23) GGGTGGTGACTTTACACGCC Antisense (SEQ ID NO: 24) GGACAAGATGCCAGGACCTG | 109 | GI6679438 |

Results

FIG. 9A illustrates the effects of caffeic acid on the morphology of rat PA during adipocyte differentiation: as seen in 3T3-L1 cells, the morphology of rat PA gradually changes during the adipocyte differentiation process, with the cells acquiring an adipocyte morphology rich in lipid droplets which starts to appear at D5. The addition of 2.2 µM caffeic acid at D0 leads to an inhibition of lipid accumulation in the cells (droplets less numerous and smaller in size).

FIG. 9B illustrates the effects of caffeic acid on aP2 expression in rat PA during adipocyte differentiation: as seen with human PA or with 3T3-L1 cells, aP2 expression increases during rat PA differentiation starting at D3 (compare the control points D0 and D3). The addition of 2.2 µM caffeic acid at D0 decreases aP2 expression at D3, which correlates with the microscopic findings (FIG. 9A).

Example 10

Overexpression of Human 15-LO in 3T3-L1 Cells Stimulates Adipocyte Differentiation Transient Transfection of 3T3-L1 Cells 3T3-L1 cells are cultivated as described in example 8. At the fibroblast stage, $3.10^5$ cells/ml of suspension are transiently transfected with 2 µg of plasmid coding for human 15-LO under the control of the aP2 promoter (plasmid ap2-15-LO) or the pBlueScript SKII+ plasmid as negative control, with the aid of the "jetPEI™" kit according to the supplier's instructions (Polyplus transfection). One milliliter of transfected cells are transferred into 12-well microtiter plates for RNA extraction and 100 µl into 96-well microtiter plates for assay of intracellular triglycerides. Two days post-transfection the cells are differentiated to mature adipocytes as described in example 8.

Triglyceride Assay

The accumulation of intracellular triglycerides at different times during adipocyte differentiation of transfected 3T3-L1 cells is determined by an improved protocol using the "TG PAP 10003" kit (bioMérieux SA, France). Briefly, cells are incubated with 20 µl isopropanol for 30 min at room temperature. Triglyceride reagent (100 µl) is then added to each well and the plates are incubated for 30 min at 37° C. Absorbance is measured on a spectrophotometer at 492 nm.

RNA Extraction and Analysis of aP2, C/EBPα and Adiponectin Expression by RT-QPCR Total RNA is extracted at different times during differentiation according to the method described in example 3 and the expression of the adipocyte differentiation markers aP2, C/EBPα and adiponectin is analyzed by RT-QPCR according to the method described in example 2 (see Table 11).

TABLE 11

| Gene | Primer sequences (5' -> 3') | Size of PCR product (bp) | Genbank number |
|---|---|---|---|
| maP2 | Sense (SEQ ID NO: 21) GTGATGCCTTTGTGGGAACCTG Antisense (SEQ ID NO: 22) TCACCTTCCTGTCGTCTGCG | 240 | NM_024406 |
| mC/EBPα | Sense (SEQ ID NO: 27) TGGACAAGAACAGCAACGAG Antisense (SEQ ID NO: 28) TCACTGGTCAACTCCAGCAC | 127 | NM_007678 |
| mAdiponectin | Sense (SEQ ID NO: 29) GATGGCAGAGATGGCACTCCTG Antisense (SEQ ID NO: 30) AGCCCCACACTGAACGCTGA | 191 | BC028770 |
| m/rCyclophilin | Sense (SEQ ID NO: 23) GGGTGGTGACTTTACACGCC Antisens (SEQ ID NO: 24) GGACAAGATGCCAGGACCTG | 109 | GI6679438 |

Adiponectin Secretion

As in the case of human primary adipocytes described in example 6, adiponectin is a marker of adipocyte differentiation in cell cultures. Adiponectin concentrations are determined in culture supernatants at different times during differentiation with the aid of a DuoSet® ELISA mouse adiponectin/ACRP30 kit according to the supplier's instructions (R&D, Minneapolis, Minn., USA).

Results

The accumulation of triglycerides in transfected 3T3-L1 cells during adipocyte differentiation is illustrated in FIG. 10A. During the differentiation process the transfected cells gradually become loaded with triglycerides. From D7 of differentiation, cells overexpressing 15-LO show a significant two-fold higher level of triglycerides than cells transfected with the control pBlueScript SKII+ plasmid.

FIG. 10B shows that overexpression of 15-LO in 3T3-L1 cells induced a highly significant increase in the expression of all the adipocyte differentiation markers tested (aP2, C/EBPα and adiponectin) as compared to the expression levels of these genes in cells transfected with the control plasmid. This significant increase appears at D3 of differentiation with regard to aP2 and C/EBPα expression. Finally, FIG. 10C shows that the increase in adiponectin expression is correlated with increased secretion thereof in cells overexpressing 15-LO as compared to cells transfected with the control plasmid.

Together these data show that overexpression of 15-LO stimulates the differentiation of 3T3-L1 cells to mature adipocytes. These results, together with the pharmacological data on inhibition of 15-LO activity described in examples 5, 6, 8 and 9, therefore confirm the pro-adipogenic role of 15-LO.

Example 11

12/15-LO Knock-Out Mice are Resistant to High Fat Diet Induced Obesity

Animal Treatment

12/15-LO knock-out mice in a C57Bl/6j genetic background were obtained from Jackson Laboratory (Bar Harbor, Me., US). Hereinafter, mice deficient for the 12/15-LO gene are referred to as LOKO mice. C57Bl/6j mice used as controls were from Charles River Laboratories (L'Arbresle, France). Animals are maintained on a 12-hour day/night cycle. For the high fat diet-induced obesity protocol, only male mice are used.

From weaning to age 7 weeks, the mice were fed ad libitum with rodent feed containing 7% fat (ref. R0310; supplier: UAR, Villemoisson, France). At 7 weeks of age, the mice (n=6 to 7 per group) are fed ad libitum with either a standard low fat diet (10.5 kcal %, ref.: D12329, supplier: Research Diets) or a diet rich in saturated fat acids (58 kcal %; ref.: D1233; supplier: Research Diets). The mice are fed these diets for 11 to 12 weeks and are weighed once a week.

Determination of Fat Mass

After 12 weeks on the diet, the fat mass of two mice in each group is determined by densitometry with the aid of a Piximus (Lunar Corp., Madison, Wis., US) in which two x-ray beams of different energies allow the measurement of fat mass (lipids), lean mass (protein and water) and bone mass. To take these measurements, the mice are anesthetized with a ketamine/xylazine mixture. After anesthesia induction, the mice are weighed and measured, and placed under the x-ray beam ventral side down. The head is not included in the different parameters measured. When the measurements are completed these mice as well as the remaining mice (n=2 to 3) are sacrificed by cervical dislocation and epididymal and perirenal AT is harvested and weighed.

Determination of Adipocyte Size

After 11 weeks on the diet, two animals in each group are sacrificed by cervical dislocation after isoflurane anesthesia. A sample of epididymal AT is taken from each mouse and fixed in 4% paraformaldehyde pH 7.4, then embedded in Tissue-Tek® OCT. The AT is then cut into 7 µm sections which are stained with hematoxylin. Adipocyte size (n=1000) is determined on a Quips Image Analysis system (Leica Mikroskopic und System GmbH, Wetzlar, Germany).

Results

The results in FIG. 11A show that LOKO mice on a high fat diet for 12 weeks gain significantly less weight than control C57Bl/6j mice. Even with the standard diet, weight gain differs between LOKO and control mice, although this difference is much smaller and did not reach statistical significance. No difference in weight gain is observed between LOKO mice on a high fat diet and those on a standard diet.

As shown in FIG. 11B, densitometric analysis of body composition indicates that fat mass in the LOKO mice is much lower than in C57Bl/6j mice, irrespective of the diet. Moreover, while the high fat diet induces an increase in fat mass in the C57Bl/6j mice, the LOKO mice on this same diet do not develop any more fat mass than those on the standard diet. FIG. 11C shows the weights of epididymal and perirenal AT in C57Bl/6j and LOKO mice on the standard or high fat diet. It can be seen that these weights are perfectly correlated with the densitometric data (FIG. 11B). The weights of epididymal and perirenal AT in LOKO mice are lower than in C57Bl/6j mice irrespective of the diet, and the high fat diet induces a significant increase in epididymal and perirenal AT weights only in the C57Bl/6j controls. These results indicate that the difference in weight, as well as in weight gain, between LOKO and C57Bl/6j mice is primarily due to a reduction in the development of adipose tissue.

FIG. 11D presents the histological findings on epididymal AT from C57Bl/6j and LOKO mice on the standard or high fat diet for 12 weeks. Adipocytes from LOKO mice on the high fat diet are noticeably smaller than those from the C57Bl/6j controls. To quantitatively measure adipose cell size, morphometric analysis of adipose tissue sections were carried out. The results in FIG. 11E show that the average size of adipocytes from LOKO mice is unaffected by the high fat diet whereas it increases significantly in epididymal AT from C57Bl/6j controls as compared to the effect seen with the standard diet.

Together these findings indicate that the absence of 12/15-LO expression, and more specifically the absence of 15-LO activity, affects the development of abdominal visceral AT and the storage of triglycerides in adipocytes in vivo and prevents the development of obesity induced by a high fat diet.

BIBLIOGRAPHY

Alberti K G, et al., *The metabolic syndrome—A new worldwide definition*, Lancet, 2005, 366 (9491), 1059-62

Auerbach B J, et al., *A spectrophotometric microtiter-based assay for the detection of hydroperoxy derivatives of linoleic acid*, Anal Biochem, 1992, 201 (2), 375-80

Bezuglov V V, et al., *Serotoninamide of arachidonic acids as an irreversible inhibitor of soybean lipoxygenase*, Bioorganicheskaya Khimiya, 1996, 22 (10-11), 878-880

Bocan T M, et al., *A specific 15-lipoxygenase inhibitor limits the progression and monocyte-macrophage enrichment of hypercholesterolemia-induced atherosclerosis in the rabbit*, Atherosclerosis, 1998, 136 (2), 203-16

Brash A R, et al., *Discovery of a second 15S-lipoxygenase in humans*, Proc Natl Acad Sci USA, 1997, 94 (12), 6148-52

Brathe A, et al., *6-substituted purines as inhibitors of 15-lipoxygenase; a structure-activity study*, Arch Pharm (Weinheim), 2005, 338 (4), 159-66

Carroll J, et al., *Probing sponge-derived terpenoids for human 15-lipoxygenase inhibitors*, J Org Chem, 2001, 66 (21), 6847-51

Cichewicz R H, et al., *Redox inactivation of human 15-lipoxygenase by marine-derived meroditerpenes and synthetic chromanes: archetypes for a unique class of selective and recyclable inhibitors*, J Am Chem Soc, 2004, 126 (45), 14910-20

Cornicelli J A and Trivedi B K, *15-Lipoxygenase and its inhibition: a novel therapeutic target for vascular disease*, CurrPharm Des, 1999, 5 (1), 11-20

Fajas L, et al., *Transcriptional control of adipogenesis*, Curr Opin Cell Biol, 1998, 10 (2), 165-73

Gan O F, et al., *Defining the arachidonic acid binding site of human 15-lipoxygenase. Molecular modeling and mutagenesis*, J Biol Chem, 1996, 271 (41), 25412-8

Gleason M M, et al., *Characterization and inhibition of 15-lipoxygenase in human monocytes: comparison with soybean 15-lipoxygenase*, Am J Physiol, 1995, 268 (5 Pt 1), C1301-7

Gundersen L, et al., *Indolizines as novel potent inhibitors of 15-lipoxygenase.*, Bioorg Med Chem, 2003, 11 (24), 5409-15

Gutierrez-Lugo M T, et al., *Lipoxygenase inhibition by anadanthoflavone, a new flavonoid from the aerial parts of Anadenanthera colubrina*, Planta Med, 2004, 70 (3), 263-5

Harats D, et al., *Overexpression of 15-lipoxygenase in vascular endothelium accelerates early atherosclerosis in LDL receptor-deficient mice*, Arterioscler Thromb Vasc Biol, 2000, 20 (9), 2100-5

Hsi L C, et al., *Opposing effects of 15-lipoxygenase-1 and -2 metabolites on MAPK signaling in prostate. Alteration in peroxisome proliferator-activated receptor gamma*, J Biol Chem, 2002, 277 (43), 40549-56

Jiang Z Y, et al., *Ferrous ion oxidation in the presence of xylenol orange for detection of lipid hydroperoxide in low density lipoprotein*, Anal Biochem, 1992, 202 (2), 384-9

Kuhn H and Borngraber S, *Mammalian 15-lipoxygenases. Enzymatic properties and biological implications*, Adv Exp Med Biol, 1999, 447 5-28

Lapidus L, et al., *Distribution of adipose tissue and risk of cardiovascular disease and death: a 12 year follow up of participants in the population study of women in Gothenburg, Sweden*, Br Med J (Clin Res Ed), 1984, 289 (6454), 1257-61

Larsson B, et al., *Abdominal adipose tissue distribution, obesity, and risk of cardiovascular disease and death: 13 year follow up of participants in the study of men born in 1913*, Br Med J (Clin Res Ed), 1984, 288 (6428), 1401-4

Lin B B and Lin y S, *Selective inhibition on 15-lipoxygenase of squalene isolated from prunus persica*, Chemistry Express, 1992, 7 (4), 297-300

Lin B B and Lin y S, *Selective inhibition on 15-lipoxygenase of trans-phytol isolated from oxalis corniculata L.*, Chemistry Express, 1993, 8 (1), 21-4

Lin B B and Lin y S, *A facile synthesis of 1-ethoxy-4-cyano-5-ethoxycarbonyl-3H-azuleno[1,2-c]pyran-3-one, a selective 15-lipoxygenase inhibitor*, Bioorganic and medicinal chemistry letters, 2004, 14 (1), 63-5

Lin B B, et al., *A facile synthesis of 1-ethoxy-4-cyano-5-ethoxycarbonyl-3H-azuleno[1,2-c]pyran-3-one, a selective 15-lipoxygenase inhibitor*, Bioorg Med Chem Lett, 2004, 14 (1), 63-5 (ndt: this appears twice in your list of references)

Lyckander I M and Malterud K E, *Lipophilic flavonoids from Orthosiphon spicatus as inhibitors of 15-lipoxygenase*, Acta Pharmaceutica Nordica, 1992, 4 (3), 159-66

Malterud K E and Rydland K M, *Inhibitors of 15-lipoxygenase from orange peel*, J Agric Food Chem, 2000, 48 (11), 5576-80

Malterud K E, et al., *Inhibition of 15-lipoxygenase by phthalate plasticizers*, Bull Environ Contam Toxicol, 1999, 62 (3), 352-5

Montero A and Badr K F, *15-Lipoxygenase in glomerular inflammation*, Exp Nephrol, 2000, 8 (1), 14-9

Rydberg E K, et al., *Hypoxia increases LDL oxidation and expression of 15-lipoxygenase-2 in human macrophages*, Arterioscier Thromb Vasc Biol, 2004, 24 (11), 2040-5

Segraves E N, et al., *Probing the activity differences of simple and complex brominated aryl compounds against 15-soybean, 15-human, and 12-human lipoxygenase*, J Med Chem, 2004, 47 (16), 4060-5

Sendobry S M, et al., *Attenuation of diet-induced atherosclerosis in rabbits with a highly selective 15-lipoxygenase inhibitor lacking significant antioxidant properties*, Br J Pharmacol, 1997, 120 (7), 1199-206

Shannon V R, et al., *Histochemical evidence for induction of arachidonate 15-lipoxygenase in airway disease*, Am Rev Respir Dis, 1993, 147 (4), 1024-8

Shillabeer G, et al., *Arachidonic acid metabolites of the lipoxygenase as well as the cyclooxygenase pathway may be involved in regulating preadipocyte differentiation*, Metabolism, 1998, 47 (4), 461-6

Shureiqi I, et al., *15-LOX-1: a novel molecular target of nonsteroidal anti-inflammatory drug-induced apoptosis in colorectal cancer cells*, J Natl Cancer Inst, 2000, 92 (14), 1136-42

Shureiqi I, et al., *15-Lipoxygenase-1 mediates nonsteroidal anti-inflammatory drug-induced apoptosis independently of cyclooxygenase-2 in colon cancer cells*, Cancer Res, 2000, 60 (24), 6846-50

Teklu S, et al., *Indolizine 1-sulfonates as potent inhibitors of 15-lipoxygenase from soybeans*, Bioorg Med Chem, 2005, 13 (9), 3127-39

Walther M, et al., *The inhibition of mammalian 15-lipoxygenases by the anti-inflammatory drug ebselen: dual-type mechanism involving covalent linkage and alteration of the iron ligand sphere*, Mol Pharmacol, 1999, 56 (1), 196-203

Watanabe T, et al., *Molecular cloning of a 12-lipoxygenase cDNA from rat brain*, Eur J Biochem, 1993, 212 (2), 605-12

Weinstein D S, et al., *Tryptamine and homotryptamine-based sulfonamides as potent and selective inhibitors of 15-lipoxygenase*, Bioorg Med Chem Lett, 2005, 15 (5), 1435-40

---

The invention claimed is:

1. A method for treating obesity comprising administering to a subject an effective amount of at least one agent that inhibits the activity of 15-lipoxygenase (15-LO) in a selective manner, wherein said agent has an $IC_{50}$ for 15-LO less than or equal to 1 μM.

2. The method of claim 1, wherein the obesity is abdominal visceral obesity.

3. The method of claim 1, wherein the 15-LO is 15-LO-1.

4. The method of claim 1, wherein said agent is 6,11-dihydro-5-thia-11-aza-benzo[a]-fluorene (PD146176).

* * * * *

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: 15-LO-1 sense primer

<400> SEQUENCE: 1
ggcaaggaga cagaactcaa ggtg                                           24

<210> SEQ ID NO 2
<211> LENGTH: 20
<212> TYPE: DNA
<213> ORGANISM: Artificial Sequence
<220> FEATURE:
<223> OTHER INFORMATION: 15-LO-1 antisense primer
```

<400> SEQUENCE: 2
cttcaggcag gctcaggacg                                        20

<210> SEQ ID NO 3
<211> LENGTH: 22
<212> TYPE: DNA
<213> ORGANISM: Artificial Sequence
<220> FEATURE:
<223> OTHER INFORMATION: cyclophilin sense primer

<400> SEQUENCE: 3
ggtgacttca cacgccataa tg                                     22

<210> SEQ ID NO 4
<211> LENGTH: 20
<212> TYPE: DNA
<213> ORGANISM: Artificial Sequence
<220> FEATURE:
<223> OTHER INFORMATION: cyclophilin antisense primer

<400> SEQUENCE: 4
tgtgttgggt ccagcatttg                                        20

<210> SEQ ID NO 5
<211> LENGTH: 22
<212> TYPE: DNA
<213> ORGANISM: Artificial Sequence
<220> FEATURE:
<223> OTHER INFORMATION: 18S sense primer

<400> SEQUENCE: 5
cggacacgga caggattgac ag                                     22

<210> SEQ ID NO 6
<211> LENGTH: 20
<212> TYPE: DNA
<213> ORGANISM: Artificial Sequence
<220> FEATURE:
<223> OTHER INFORMATION: 18s antisense primer

<400> SEQUENCE: 6
aatctcgggt ggctgaacgc                                        20

<210> SEQ ID NO 7
<211> LENGTH: 25
<212> TYPE: DNA
<213> ORGANISM: Artificial Sequence
<220> FEATURE:
<223> OTHER INFORMATION: 36B4 sense primer

<400> SEQUENCE: 7
catgctcaac atctcccect tctcc                                  25

<210> SEQ ID NO 8
<211> LENGTH: 25
<212> TYPE: DNA
<213> ORGANISM: Artificial Sequence
<220> FEATURE:
<223> OTHER INFORMATION: 36B4 antisense primer

<400> SEQUENCE: 8
gggaaggtgt aatccgtctc cacag                                  25

<210> SEQ ID NO 9
<211> LENGTH: 18
<212> TYPE: DNA

```
<213> ORGANISM: Artificial Sequence
<220> FEATURE:
<223> OTHER INFORMATION: 5-LO sense primer

<400> SEQUENCE: 9
gctcatctgc gagtgtgg                                              18

<210> SEQ ID NO 10
<211> LENGTH: 19
<212> TYPE: DNA
<213> ORGANISM: Artificial Sequence
<220> FEATURE:
<223> OTHER INFORMATION: 5-LO antisense primer

<400> SEQUENCE: 10
ggaggcatag gtcaggtcc                                             19

<210> SEQ ID NO 11
<211> LENGTH: 18
<212> TYPE: DNA
<213> ORGANISM: Artificial Sequence
<220> FEATURE:
<223> OTHER INFORMATION: 12-LO sense primer

<400> SEQUENCE: 11
cctgtctcct tccagtcc                                              18

<210> SEQ ID NO 12
<211> LENGTH: 20
<212> TYPE: DNA
<213> ORGANISM: Artificial Sequence
<220> FEATURE:
<223> OTHER INFORMATION: 12-LO antisense primer

<400> SEQUENCE: 12
tcgtcacatc ttccttggtg                                            20

<210> SEQ ID NO 13
<211> LENGTH: 21
<212> TYPE: DNA
<213> ORGANISM: Artificial Sequence
<220> FEATURE:
<223> OTHER INFORMATION: aP2 sense primer

<400> SEQUENCE: 13
ggccaggaat ttgacgaagt c                                          21

<210> SEQ ID NO 14
<211> LENGTH: 26
<212> TYPE: DNA
<213> ORGANISM: Artificial Sequence
<220> FEATURE:
<223> OTHER INFORMATION: aP2 antisense primer

<400> SEQUENCE: 14
acagaatgtt gtagagttca atgcga                                     26

<210> SEQ ID NO 15
<211> LENGTH: 24
<212> TYPE: DNA
<213> ORGANISM: Artificial Sequence
<220> FEATURE:
<223> OTHER INFORMATION: r12/15-LO sense primer

<400> SEQUENCE: 15
ggctccaaca acgaggtcta cctg                                       24
```

```
<210> SEQ ID NO 16
<211> LENGTH: 20
<212> TYPE: DNA
<213> ORGANISM: Artificial Sequence
<220> FEATURE:
<223> OTHER INFORMATION: r12/15-LO antisense primer

<400> SEQUENCE: 16
aaccaggcgt catccgtgag                                              20

<210> SEQ ID NO 17
<211> LENGTH: 24
<212> TYPE: DNA
<213> ORGANISM: Artificial Sequence
<220> FEATURE:
<223> OTHER INFORMATION: m12/15-LO sense primer

<400> SEQUENCE: 17
ggctccaaca acgaggtcta cctg                                         24

<210> SEQ ID NO 18
<211> LENGTH: 20
<212> TYPE: DNA
<213> ORGANISM: Artificial Sequence
<220> FEATURE:
<223> OTHER INFORMATION: m12/15-LO antisense primer

<400> SEQUENCE: 18
gagagtcttc aaccacggtg                                              20

<210> SEQ ID NO 19
<211> LENGTH: 20
<212> TYPE: DNA
<213> ORGANISM: Artificial Sequence
<220> FEATURE:
<223> OTHER INFORMATION: mLPL sense primer

<400> SEQUENCE: 19
actgccactt caaccacagc                                              20

<210> SEQ ID NO 20
<211> LENGTH: 20
<212> TYPE: DNA
<213> ORGANISM: Artificial Sequence
<220> FEATURE:
<223> OTHER INFORMATION: mLPL antisense primer

<400> SEQUENCE: 20
actcctcctc catccagttg                                              20

<210> SEQ ID NO 21
<211> LENGTH: 22
<212> TYPE: DNA
<213> ORGANISM: Artificial Sequence
<220> FEATURE:
<223> OTHER INFORMATION: maP2 sense primer

<400> SEQUENCE: 21
gtgatgcctt tgtgggaacc tg                                           22

<210> SEQ ID NO 22
<211> LENGTH: 20
<212> TYPE: DNA
<213> ORGANISM: Artificial Sequence
<220> FEATURE:
<223> OTHER INFORMATION: maP2 antisense primer
```

-continued

```
<400> SEQUENCE: 22
tcaccttcct gtcgtctgcg                                               20

<210> SEQ ID NO 23
<211> LENGTH: 20
<212> TYPE: DNA
<213> ORGANISM: Artificial Sequence
<220> FEATURE:
<223> OTHER INFORMATION: m/rCyclophilin sense primer

<400> SEQUENCE: 23
gggtggtgac tttacacgcc                                               20

<210> SEQ ID NO 24
<211> LENGTH: 20
<212> TYPE: DNA
<213> ORGANISM: Artificial Sequence
<220> FEATURE:
<223> OTHER INFORMATION: m/rCyclophiln antisense primer

<400> SEQUENCE: 24
ggacaagatg ccaggacctg                                               20

<210> SEQ ID NO 25
<211> LENGTH: 20
<212> TYPE: DNA
<213> ORGANISM: Artificial Sequence
<220> FEATURE:
<223> OTHER INFORMATION: raP2 sense primer

<400> SEQUENCE: 25
aactcgtctc cagtgagaac                                               20

<210> SEQ ID NO 26
<211> LENGTH: 20
<212> TYPE: DNA
<213> ORGANISM: Artificial Sequence
<220> FEATURE:
<223> OTHER INFORMATION: raP2 antisense primer

<400> SEQUENCE: 26
atgctcttca ctttcctgtc                                               20

<210> SEQ ID NO 27
<211> LENGTH: 20
<212> TYPE: DNA
<213> ORGANISM: Artificial Sequence
<220> FEATURE:
<223> OTHER INFORMATION: C/EBP-alpha sense primer

<400> SEQUENCE: 27
tggacaagaa cagcaacgag                                               20

<210> SEQ ID NO 28
<211> LENGTH: 20
<212> TYPE: DNA
<213> ORGANISM: Artificial Sequence
<220> FEATURE:
<223> OTHER INFORMATION: C/EBP-alpha antisense primer

<400> SEQUENCE: 28
tcactggtca actccagcac                                               20

<210> SEQ ID NO 29
<211> LENGTH: 22
<212> TYPE: DNA
```

```
<213> ORGANISM: Artificial Sequence
<220> FEATURE:
<223> OTHER INFORMATION: mAdiponectin sense primer

<400> SEQUENCE: 29
gatggcagag atggcactcc tg                                          22

<210> SEQ ID NO 30
<211> LENGTH: 20
<212> TYPE: DNA
<213> ORGANISM: Artificial Sequence
<220> FEATURE:
<223> OTHER INFORMATION: mAdiponectin antisense primer

<400> SEQUENCE: 30
agccccacac tgaacgctga                                             20
```